(12) United States Patent
Rashbaum et al.

(10) Patent No.: US 10,492,919 B2
(45) Date of Patent: *Dec. 3, 2019

(54) INTERVERTEBRAL DISC PROSTHESIS

(71) Applicant: LDR Medical, Sainte-Savine (FR)

(72) Inventors: Ralph Rashbaum, Plano, TX (US);
Kee D. Kim, Davis, CA (US); Hyun Bae, Santa Monica, CA (US)

(73) Assignee: LDR Medical, Rosieres Pres Troyes (FR)

( * ) Notice: Subject to any disclaimer, the term of this patent is extended or adjusted under 35 U.S.C. 154(b) by 60 days.

This patent is subject to a terminal disclaimer.

(21) Appl. No.: 15/464,639

(22) Filed: Mar. 21, 2017

(65) Prior Publication Data

US 2017/0252179 A1 Sep. 7, 2017

Related U.S. Application Data

(63) Continuation of application No. 14/659,587, filed on Mar. 16, 2015, now Pat. No. 9,597,194, which is a
(Continued)

(30) Foreign Application Priority Data

Sep. 23, 2005 (FR) ..................... 05 09740

(51) Int. Cl.
*A61F 2/44* (2006.01)
*A61F 2/30* (2006.01)
*A61B 17/064* (2006.01)

(52) U.S. Cl.
CPC ........ *A61F 2/4425* (2013.01); *A61F 2/30749* (2013.01); *A61B 17/0642* (2013.01);
(Continued)

(58) Field of Classification Search
CPC .................. A61F 2/4425; A61F 2002/443
See application file for complete search history.

(56) References Cited

U.S. PATENT DOCUMENTS 344,683 A 6/1886 Sherer
1,025,596 A 5/1912 Strawser
(Continued)

FOREIGN PATENT DOCUMENTS

CA 2472708 A1 2/2005
CA 2622028 A1 3/2007
(Continued)

OTHER PUBLICATIONS

"U.S. Appl. No. 10/476,565, Amendment After Final filed Nov. 29, 2007", 1 pg.
(Continued)

*Primary Examiner* — Ellen C Hammond
(74) *Attorney, Agent, or Firm* — Schwegman Lundberg & Woessner, P.A.

(57) ABSTRACT

An intervertebral disc prosthesis is disclosed comprising at least two plates, namely first and second plates, articulated about each other by means of a curved surface, namely articulation, of at least one of the plates, each of the plates comprising a surface known as a contact surface, intended to be in contact with a vertebral plate of one of the vertebrae between which the prosthesis is intended to be inserted, this contact surface for each of the plates comprising a geometrical centre at equal distance from at least two diametrically opposite points located on the periphery of the plate, in which the geometric centres of the plates are not vertically aligned, this off-setting of the geometrical centres of the plates engendering an off-setting of the edges of the plates in at least one direction perpendicular to the vertical axis of the spinal column.

8 Claims, 4 Drawing Sheets

Related U.S. Application Data continuation of application No. 12/955,898, filed on Nov. 29, 2010, now Pat. No. 8,979,932, which is a continuation of application No. 11/341,007, filed on Jan. 27, 2006, now Pat. No. 7,842,088.

(52) U.S. Cl.
CPC ... *A61B 2017/0647* (2013.01); *A61F 2/30734* (2013.01); *A61F 2002/305* (2013.01); *A61F 2002/30331* (2013.01); *A61F 2002/30365* (2013.01); *A61F 2002/30369* (2013.01); *A61F 2002/30576* (2013.01); *A61F 2002/30616* (2013.01); *A61F 2002/30662* (2013.01); *A61F 2002/30878* (2013.01); *A61F 2002/30884* (2013.01); *A61F 2002/30904* (2013.01); *A61F 2002/443* (2013.01); *A61F 2220/0016* (2013.01); *A61F 2220/0025* (2013.01); *A61F 2220/0033* (2013.01)

(56) References Cited

U.S. PATENT DOCUMENTS

| | | |
|---|---|---|
| 1,121,484 A | 12/1914 | Crites |
| 1,436,573 A | 11/1922 | Joseph |
| 2,836,442 A | 5/1958 | Moskovitz |
| 3,325,197 A | 6/1967 | Wehner |
| 3,374,786 A | 3/1968 | Callender, Jr. |
| 3,486,505 A | 12/1969 | Morrison |
| 3,791,380 A | 2/1974 | Dawidowski |
| 3,857,642 A | 12/1974 | Miller |
| 3,875,595 A | 4/1975 | Froning |
| 3,892,232 A | 7/1975 | Neufeld |
| 3,948,262 A | 4/1976 | Zaffaroni |
| 3,958,278 A | 5/1976 | Lee et al. |
| 4,009,712 A | 3/1977 | Burstein et al. |
| 4,074,542 A | 2/1978 | Hankosky et al. |
| 4,085,466 A | 4/1978 | Goodfellow et al. |
| 4,135,506 A | 1/1979 | Ulrich |
| 4,175,555 A | 11/1979 | Herbert |
| 4,185,762 A | 1/1980 | Froehlich |
| 4,237,875 A | 12/1980 | Termanini |
| 4,309,777 A | 1/1982 | Patil |
| 4,349,921 A | 9/1982 | Kuntz |
| 4,379,451 A | 4/1983 | Getscher |
| 4,409,974 A | 10/1983 | Freedland et al. |
| 4,432,358 A | 2/1984 | Fixel |
| 4,488,543 A | 12/1984 | Tornier |
| 4,494,535 A | 1/1985 | Haig |
| 4,507,115 A | 3/1985 | Kambara et al. |
| 4,519,100 A | 5/1985 | Wills et al. |
| 4,561,432 A | 12/1985 | Mazor |
| 4,599,086 A | 7/1986 | Doty |
| 4,612,920 A | 9/1986 | Lower |
| 4,621,629 A | 11/1986 | Koeneman |
| 4,632,101 A | 12/1986 | Freedland |
| 4,653,489 A | 3/1987 | Tronzo |
| 4,655,778 A | 4/1987 | Koeneman |
| 4,657,001 A | 4/1987 | Fixel |
| 4,664,305 A | 5/1987 | Blake, III et al. |
| 4,714,469 A | 12/1987 | Kenna |
| 4,721,103 A | 1/1988 | Freedland |
| 4,756,711 A | 7/1988 | Mai et al. |
| 4,759,352 A | 7/1988 | Lozier |
| 4,759,766 A | 7/1988 | Buettner-janz et al. |
| 4,759,769 A | 7/1988 | Hedman et al. |
| 4,787,378 A | 11/1988 | Sodhi |
| 4,787,908 A | 11/1988 | Wyss et al. |
| 4,790,303 A | 12/1988 | Steffee |
| 4,791,918 A | 12/1988 | Von Hasselbach |
| 4,834,757 A | 5/1989 | Brantigan |
| 4,863,476 A | 9/1989 | Shepperd |
| 4,874,389 A | 10/1989 | Downey |
| 4,892,545 A | 1/1990 | Day et al. |
| 4,898,156 A | 2/1990 | Gatturna et al. |
| 4,904,261 A | 2/1990 | Dove et al. |
| 4,911,718 A | 3/1990 | Lee et al. |
| 4,932,975 A | 6/1990 | Main et al. |
| 4,946,378 A | 8/1990 | Hirayama et al. |
| 4,946,468 A | 8/1990 | Li |
| 4,955,908 A | 9/1990 | Frey et al. |
| 4,955,916 A | 9/1990 | Carignan et al. |
| 4,964,403 A | 10/1990 | Karas et al. |
| 4,968,315 A | 11/1990 | Gatturna |
| 4,969,887 A | 11/1990 | Sodhi |
| 4,973,332 A | 11/1990 | Kummer |
| 4,973,333 A | 11/1990 | Treharne |
| 4,997,432 A | 3/1991 | Keller |
| 5,002,550 A | 3/1991 | Li |
| 5,002,576 A | 3/1991 | Fuhrmann et al. |
| 5,007,910 A | 4/1991 | Anapliotis et al. |
| 5,032,125 A | 7/1991 | Durham et al. |
| 5,041,114 A | 8/1991 | Chapman et al. |
| 5,041,116 A | 8/1991 | Wilson |
| 5,041,139 A | 8/1991 | Branemark |
| 5,046,513 A | 9/1991 | Gatturna et al. |
| 5,057,103 A | 10/1991 | Davis |
| 5,062,851 A | 11/1991 | Branemark |
| 5,071,437 A | 12/1991 | Steffee |
| 5,087,266 A | 2/1992 | Connell et al. |
| 5,098,433 A | 3/1992 | Freedland |
| 5,116,336 A | 5/1992 | Frigg |
| 5,122,130 A | 6/1992 | Keller |
| 5,123,926 A | 6/1992 | Pisharodi |
| 5,129,901 A | 7/1992 | Decoste |
| 5,171,281 A | 12/1992 | Parsons et al. |
| 5,176,681 A | 1/1993 | Lawes et al. |
| 5,192,303 A | 3/1993 | Gatturna et al. |
| 5,192,327 A | 3/1993 | Brantigan |
| 5,197,986 A | 3/1993 | Mikhail |
| 5,207,679 A | 5/1993 | Li |
| 5,217,486 A | 6/1993 | Rice et al. |
| 5,234,447 A | 8/1993 | Kaster et al. |
| 5,242,448 A | 9/1993 | Pettine et al. |
| 5,246,458 A | 9/1993 | Graham |
| 5,258,009 A | 11/1993 | Conners |
| 5,258,031 A | 11/1993 | Salib et al. |
| 5,290,312 A | 3/1994 | Kojimoto |
| 5,300,074 A | 4/1994 | Frigg |
| 5,306,307 A | 4/1994 | Senter et al. |
| 5,306,309 A | 4/1994 | Wagner et al. |
| 5,314,477 A | 5/1994 | Marnay |
| 5,324,292 A | 6/1994 | Meyers |
| 5,326,205 A | 7/1994 | Anspach, Jr. et al. |
| 5,342,394 A | 8/1994 | Matsuno et al. |
| 5,356,410 A | 10/1994 | Pennig |
| 5,356,413 A | 10/1994 | Martins et al. |
| 5,358,526 A | 10/1994 | Tornier |
| 5,370,697 A | 12/1994 | Baumgartner |
| 5,372,599 A | 12/1994 | Martins |
| 5,397,364 A | 3/1995 | Kozak et al. |
| 5,401,269 A | 3/1995 | Buttner-janz et al. |
| 5,417,692 A | 5/1995 | Goble et al. |
| 5,417,712 A | 5/1995 | Whittaker et al. |
| 5,425,772 A | 6/1995 | Brantigan |
| 5,425,773 A | 6/1995 | Boyd et al. |
| 5,429,641 A | 7/1995 | Gotfried |
| 5,437,674 A | 8/1995 | Worcel |
| 5,443,514 A | 8/1995 | Steffee |
| 5,452,499 A | 9/1995 | Schmidt et al. |
| 5,456,721 A | 10/1995 | Legrand |
| 5,458,601 A | 10/1995 | Young, Jr. et al. |
| 5,458,638 A | 10/1995 | Kuslich et al. |
| 5,472,452 A | 12/1995 | Trott |
| 5,478,342 A | 12/1995 | Kohrs |
| 5,489,210 A | 2/1996 | Hanosh |
| 5,501,695 A | 3/1996 | Anspach, Jr. et al. |
| 5,507,754 A | 4/1996 | Green et al. |
| 5,507,816 A | 4/1996 | Bullivant |
| 5,522,845 A | 6/1996 | Wenstrom, Jr. |
| 5,522,899 A | 6/1996 | Michelson |
| 5,531,792 A | 7/1996 | Huene |
| 5,534,004 A | 7/1996 | Santangelo |

(56) References Cited

U.S. PATENT DOCUMENTS

| | | |
|---|---|---|
| 5,534,029 A | 7/1996 | Shima |
| 5,534,030 A | 7/1996 | Navarro et al. |
| 566,360 A | 8/1996 | White |
| 5,545,229 A | 8/1996 | Parsons et al. |
| 5,549,617 A | 8/1996 | Green et al. |
| 5,554,191 A | 9/1996 | Lahille et al. |
| 5,556,431 A | 9/1996 | Buttner-janz |
| 5,562,689 A | 10/1996 | Green et al. |
| 5,562,738 A | 10/1996 | Boyd et al. |
| 5,571,104 A | 11/1996 | Li |
| 5,571,109 A | 11/1996 | Bertagnoli |
| 5,571,189 A | 11/1996 | Kuslich |
| 5,578,035 A | 11/1996 | Lin |
| 5,591,168 A | 1/1997 | Judet et al. |
| 5,593,409 A | 1/1997 | Michelson |
| 5,609,635 A | 3/1997 | Michelson |
| 5,609,636 A | 3/1997 | Kohrs et al. |
| 5,613,974 A | 3/1997 | Andreas et al. |
| 5,620,012 A | 4/1997 | Benderev et al. |
| 5,643,321 A | 7/1997 | Mcdevitt |
| 5,645,596 A | 7/1997 | Kim et al. |
| 5,655,698 A | 8/1997 | Yoon |
| 5,658,335 A | 8/1997 | Allen |
| 5,674,294 A | 10/1997 | Bainville et al. |
| 5,676,701 A | 10/1997 | Yuan et al. |
| 5,676,702 A | 10/1997 | Ratron |
| 5,683,394 A | 11/1997 | Rinner |
| 5,683,464 A | 11/1997 | Wagner et al. |
| 5,683,465 A | 11/1997 | Shinn et al. |
| 5,702,449 A | 12/1997 | Mckay |
| 5,702,450 A | 12/1997 | Bisserie |
| 5,702,472 A | 12/1997 | Huebner |
| 5,713,899 A | 2/1998 | Marnay et al. |
| 5,722,977 A | 3/1998 | Wilhelmy |
| 5,741,253 A | 4/1998 | Michelson |
| 5,755,798 A | 5/1998 | Papavero et al. |
| 5,766,252 A | 6/1998 | Henry et al. |
| 5,766,253 A | 6/1998 | Brosnahan, III |
| 5,772,661 A | 6/1998 | Michelson |
| 5,776,199 A | 7/1998 | Michelson |
| 5,782,830 A | 7/1998 | Farris |
| 5,782,832 A | 7/1998 | Larsen et al. |
| 5,782,919 A | 7/1998 | Zdeblick et al. |
| 5,797,909 A | 8/1998 | Michelson |
| 5,800,547 A | 9/1998 | Schafer et al. |
| 5,800,550 A | 9/1998 | Sertich |
| 5,807,403 A | 9/1998 | Beyar et al. |
| 5,810,820 A | 9/1998 | Santori et al. |
| 5,824,094 A | 10/1998 | Serhan et al. |
| 5,827,328 A | 12/1998 | Buttermann |
| 5,849,004 A | 12/1998 | Bramlet |
| 5,860,973 A | 1/1999 | Michelson |
| 5,865,845 A | 2/1999 | Thalgott |
| 5,865,848 A | 2/1999 | Baker |
| 5,888,222 A | 3/1999 | Coates et al. |
| 5,888,223 A | 3/1999 | Bray, Jr. |
| 5,888,224 A | 3/1999 | Beckers et al. |
| 5,888,226 A | 3/1999 | Rogozinski |
| 5,888,227 A | 3/1999 | Cottle |
| 5,888,228 A | 3/1999 | Knothe et al. |
| 5,893,889 A | 4/1999 | Harrington |
| 5,895,427 A | 4/1999 | Kuslich et al. |
| 5,895,428 A | 4/1999 | Berry |
| 5,899,941 A | 5/1999 | Nishijima et al. |
| 5,968,098 A | 10/1999 | Winslow |
| 5,976,139 A | 11/1999 | Bramlet |
| 5,980,522 A | 11/1999 | Koros et al. |
| 5,984,967 A | 11/1999 | Zdeblick et al. |
| 5,989,289 A | 11/1999 | Coates et al. |
| 6,001,130 A | 12/1999 | Bryan et al. |
| 6,010,502 A | 1/2000 | Bagby |
| 6,033,438 A | 3/2000 | Bianchi et al. |
| 6,039,763 A | 3/2000 | Shelokov |
| 6,045,552 A | 4/2000 | Zucherman et al. |
| 6,045,579 A | 4/2000 | Hochshuler et al. |
| 6,059,787 A | 5/2000 | Allen |
| 6,063,088 A | 5/2000 | Winslow |
| 6,063,121 A | 5/2000 | Xavier et al. |
| 6,066,174 A | 5/2000 | Farris |
| 6,066,175 A | 5/2000 | Henderson et al. |
| 6,080,158 A | 6/2000 | Lin |
| 6,080,193 A | 6/2000 | Hochshuler et al. |
| 6,093,205 A | 7/2000 | Mcleod et al. |
| 6,096,038 A | 8/2000 | Michelson |
| 6,096,080 A | 8/2000 | Nicholson et al. |
| 6,099,531 A | 8/2000 | Bonutti |
| 6,102,950 A | 8/2000 | Vaccaro |
| 6,111,164 A | 8/2000 | Rainey et al. |
| 6,113,637 A | 9/2000 | Gill et al. |
| 6,113,638 A | 9/2000 | Williams et al. |
| 6,120,502 A | 9/2000 | Michelson |
| 6,123,705 A | 9/2000 | Michelson |
| 6,129,763 A | 10/2000 | Chauvin et al. |
| 6,136,031 A | 10/2000 | Middleton |
| 6,143,032 A | 11/2000 | Schafer et al. |
| 6,146,421 A | 11/2000 | Gordon et al. |
| 6,146,422 A | 11/2000 | Lawson |
| 6,149,650 A | 11/2000 | Michelson |
| 6,156,067 A | 12/2000 | Bryan et al. |
| 6,174,311 B1 | 1/2001 | Branch et al. |
| 6,179,873 B1 | 1/2001 | Zientek |
| 6,179,874 B1 | 1/2001 | Cauthen |
| 6,179,875 B1 | 1/2001 | Von Strempel |
| 6,183,474 B1 | 2/2001 | Bramlet et al. |
| 6,193,757 B1 | 2/2001 | Foley et al. |
| 6,206,922 B1 | 3/2001 | Zdeblick et al. |
| 6,206,923 B1 | 3/2001 | Boyd et al. |
| 6,210,412 B1 | 4/2001 | Michelson |
| 6,210,442 B1 | 4/2001 | Wing et al. |
| 6,214,050 B1 | 4/2001 | Huene |
| 6,221,077 B1 | 4/2001 | Rinner et al. |
| 6,224,595 B1 | 5/2001 | Michelson |
| 6,224,607 B1 | 5/2001 | Michelson |
| 6,228,118 B1 | 5/2001 | Gordon |
| 6,231,609 B1 | 5/2001 | Mehdizadeh |
| 6,231,610 B1 | 5/2001 | Geisler |
| 6,235,059 B1 | 5/2001 | Benezech et al. |
| 6,241,733 B1 | 6/2001 | Nicholson et al. |
| 6,241,769 B1 | 6/2001 | Nicholson et al. |
| 6,241,770 B1 | 6/2001 | Michelson |
| 6,245,072 B1 | 6/2001 | Zdeblick et al. |
| 6,245,108 B1 | 6/2001 | Biscup |
| 6,251,140 B1 | 6/2001 | Marino et al. |
| 6,258,089 B1 | 7/2001 | Campbell et al. |
| 6,258,094 B1 | 7/2001 | Nicholson et al. |
| 6,258,125 B1 | 7/2001 | Paul et al. |
| 6,261,293 B1 | 7/2001 | Nicholson et al. |
| 6,261,295 B1 | 7/2001 | Nicholson et al. |
| 6,264,656 B1 | 7/2001 | Michelson |
| 6,267,763 B1 | 7/2001 | Castro |
| 6,267,764 B1 | 7/2001 | Elberg |
| 6,270,498 B1 | 8/2001 | Michelson et al. |
| 6,277,149 B1 | 8/2001 | Boyle et al. |
| 6,283,998 B1 | 9/2001 | Eaton |
| 6,287,308 B1 | 9/2001 | Betz et al. |
| 6,296,664 B1 | 10/2001 | Middleton |
| 6,302,914 B1 | 10/2001 | Michelson |
| 6,306,170 B2 | 10/2001 | Ray |
| 6,315,797 B1 | 11/2001 | Middleton |
| 6,319,257 B1 | 11/2001 | Carignan et al. |
| 6,342,074 B1 | 1/2002 | Simpson |
| 6,344,057 B1 | 2/2002 | Rabbe et al. |
| 6,348,071 B1 | 2/2002 | Steffee et al. |
| 6,350,283 B1 | 2/2002 | Michelson |
| 6,364,880 B1 | 4/2002 | Michelson |
| 6,368,350 B1 | 4/2002 | Erickson et al. |
| 6,371,987 B1 | 4/2002 | Weiland et al. |
| 6,371,988 B1 | 4/2002 | Pafford et al. |
| 6,375,655 B1 | 4/2002 | Zdeblick et al. |
| 6,383,186 B1 | 5/2002 | Michelson |
| 6,387,130 B1 | 5/2002 | Stone et al. |
| 6,395,031 B1 | 5/2002 | Foley et al. |
| 6,395,035 B2 | 5/2002 | Bresina et al. |
| 6,402,750 B1 | 6/2002 | Atkinson et al. |

(56) References Cited

U.S. PATENT DOCUMENTS

| | | |
|---|---|---|
| 6,402,785 B1 | 6/2002 | Zdeblick et al. |
| 6,409,765 B1 | 6/2002 | Bianchi et al. |
| 6,413,278 B1 | 7/2002 | Marchosky |
| 6,416,551 B1 | 7/2002 | Keller |
| 6,419,703 B1 | 7/2002 | Fallin et al. |
| 6,419,704 B1 | 7/2002 | Ferree |
| 6,419,706 B1 | 7/2002 | Graf |
| 6,423,063 B1 | 7/2002 | Bonutti |
| 6,423,095 B1 | 7/2002 | Van Hoeck et al. |
| 6,432,106 B1 | 8/2002 | Fraser |
| 6,432,107 B1 | 8/2002 | Ferree |
| 6,440,168 B1 | 8/2002 | Cauthen |
| 6,447,512 B1 | 9/2002 | Landry et al. |
| 6,447,544 B1 | 9/2002 | Michelson |
| 6,447,546 B1 | 9/2002 | Bramlet et al. |
| 6,447,547 B1 | 9/2002 | Michelson |
| 6,454,769 B2 | 9/2002 | Wagner et al. |
| 6,458,159 B1 | 10/2002 | Thalgott |
| 6,461,359 B1 | 10/2002 | Tribus |
| 6,468,310 B1 | 10/2002 | Ralph et al. |
| 6,471,724 B2 | 10/2002 | Zdeblick et al. |
| 6,478,800 B1 | 11/2002 | Fraser et al. |
| 6,478,823 B1 | 11/2002 | Michelson |
| 6,482,233 B1 | 11/2002 | Aebi et al. |
| 6,482,234 B1 | 11/2002 | Weber et al. |
| 6,482,584 B1 | 11/2002 | Mills et al. |
| 6,485,517 B1 | 11/2002 | Michelson |
| 6,497,726 B1 | 12/2002 | Carter et al. |
| 6,500,205 B1 | 12/2002 | Michelson |
| 6,506,216 B1 | 1/2003 | McCue et al. |
| 6,514,260 B1 | 2/2003 | Zdeblick et al. |
| 6,517,580 B1 | 2/2003 | Ramadan et al. |
| 6,520,967 B1 | 2/2003 | Cauthen |
| 6,520,996 B1 | 2/2003 | Manasas et al. |
| 6,524,312 B2 | 2/2003 | Landry et al. |
| 6,527,803 B1 | 3/2003 | Crozet et al. |
| 6,527,804 B1 | 3/2003 | Gauchet et al. |
| 6,527,806 B2 | 3/2003 | Ralph et al. |
| 6,540,753 B2 | 4/2003 | Cohen |
| 6,540,785 B1 | 4/2003 | Gill et al. |
| 6,554,863 B2 | 4/2003 | Paul et al. |
| 6,558,423 B1 | 5/2003 | Michelson |
| 6,558,424 B2 | 5/2003 | Thalgott |
| 6,565,605 B2 | 5/2003 | Goble et al. |
| 6,572,653 B1 | 6/2003 | Simonson |
| 6,576,016 B1 | 6/2003 | Hochshuler et al. |
| 6,579,291 B1 | 6/2003 | Keith et al. |
| 6,579,320 B1 | 6/2003 | Gauchet et al. |
| 6,582,468 B1 | 6/2003 | Gauchet |
| 6,592,624 B1 | 7/2003 | Fraser et al. |
| 6,599,294 B2 | 7/2003 | Fuss et al. |
| 6,599,320 B1 | 7/2003 | Kuslich |
| 6,605,089 B1 | 8/2003 | Michelson |
| 6,607,530 B1 | 8/2003 | Carl et al. |
| 6,607,558 B2 | 8/2003 | Kuras |
| 6,610,065 B1 | 8/2003 | Branch et al. |
| 6,610,089 B1 | 8/2003 | Liu et al. |
| 6,610,092 B2 | 8/2003 | Ralph et al. |
| 6,610,093 B1 | 8/2003 | Pisharodi |
| 6,613,091 B1 | 9/2003 | Zdeblick et al. |
| 6,613,278 B1 | 9/2003 | Mills et al. |
| 6,616,671 B2 | 9/2003 | Landry et al. |
| 6,620,163 B1 | 9/2003 | Michelson |
| 6,635,086 B2 | 10/2003 | Lin |
| 6,635,087 B2 | 10/2003 | Angelucci et al. |
| 6,636,071 B1 | 10/2003 | Yatabe |
| 6,641,614 B1 | 11/2003 | Wagner et al. |
| 6,645,206 B1 | 11/2003 | Zdeblick et al. |
| 6,645,249 B2 | 11/2003 | Ralph et al. |
| 6,648,893 B2 | 11/2003 | Dudasik |
| 6,652,533 B2 | 11/2003 | O'neil |
| 6,652,584 B2 | 11/2003 | Michelson |
| 6,652,586 B2 | 11/2003 | Hunter et al. |
| 6,652,818 B1 | 11/2003 | Mills et al. |
| 6,656,224 B2 | 12/2003 | Middleton |
| 6,660,038 B2 | 12/2003 | Boyer, II et al. |
| 6,666,890 B2 | 12/2003 | Michelson |
| 6,669,730 B2 | 12/2003 | Ralph et al. |
| 6,669,731 B2 | 12/2003 | Ralph et al. |
| 6,669,732 B2 | 12/2003 | Serhan et al. |
| 6,673,113 B2 | 1/2004 | Ralph et al. |
| 6,676,703 B2 | 1/2004 | Biscup |
| 6,679,887 B2 | 1/2004 | Nicholson et al. |
| 6,679,915 B1 | 1/2004 | Cauthen |
| 6,682,562 B2 | 1/2004 | Viart et al. |
| 6,695,846 B2 | 2/2004 | Richelsoph et al. |
| 6,695,851 B2 | 2/2004 | Zdeblick et al. |
| 6,695,882 B2 | 2/2004 | Bianchi et al. |
| 6,706,067 B2 | 3/2004 | Shimp et al. |
| 6,706,068 B2 | 3/2004 | Ferree |
| 6,709,439 B2 | 3/2004 | Rogers et al. |
| 6,709,458 B2 | 3/2004 | Michelson |
| 6,712,818 B1 | 3/2004 | Michelson |
| 6,716,247 B2 | 4/2004 | Michelson |
| 6,719,794 B2 | 4/2004 | Gerber et al. |
| 6,723,127 B2 | 4/2004 | Ralph et al. |
| 6,723,128 B2 | 4/2004 | Uk |
| 6,726,720 B2 | 4/2004 | Ross et al. |
| 6,730,088 B2 | 5/2004 | Yeh |
| 6,733,504 B2 | 5/2004 | Lin et al. |
| 6,733,531 B1 | 5/2004 | Trieu |
| 6,733,532 B1 | 5/2004 | Gauchet et al. |
| 6,733,535 B2 | 5/2004 | Michelson |
| 6,736,850 B2 | 5/2004 | Davis |
| 6,740,117 B2 | 5/2004 | Ralph et al. |
| 6,740,118 B2 | 5/2004 | Eisermann et al. |
| 6,743,255 B2 | 6/2004 | Ferree |
| 6,743,256 B2 | 6/2004 | Mason |
| 6,743,257 B2 | 6/2004 | Castro |
| 6,749,635 B1 | 6/2004 | Bryan |
| 6,749,636 B2 | 6/2004 | Michelson |
| 6,752,832 B2 | 6/2004 | Neumann |
| 6,755,841 B2 | 6/2004 | Fraser et al. |
| 6,758,849 B1 | 7/2004 | Michelson |
| 6,764,512 B2 | 7/2004 | Keller |
| 6,764,515 B2 | 7/2004 | Ralph et al. |
| 6,767,367 B1 | 7/2004 | Michelson |
| 6,770,074 B2 | 8/2004 | Michelson |
| 6,770,095 B2 | 8/2004 | Grinberg et al. |
| 6,770,096 B2 | 8/2004 | Bolger et al. |
| 6,793,678 B2 | 9/2004 | Hawkins |
| 6,793,679 B2 | 9/2004 | Michelson |
| RE38,614 E | 10/2004 | Paul et al. |
| 6,800,092 B1 | 10/2004 | Williams et al. |
| 6,800,093 B2 | 10/2004 | Nicholson et al. |
| 6,805,713 B1 | 10/2004 | Carter et al. |
| 6,805,714 B2 | 10/2004 | Sutcliffe |
| 6,808,537 B2 | 10/2004 | Michelson |
| 6,814,737 B2 | 11/2004 | Cauthen |
| 6,824,565 B2 | 11/2004 | Muhanna et al. |
| 6,835,206 B2 | 12/2004 | Jackson |
| 6,849,093 B2 | 2/2005 | Michelson |
| 6,890,355 B2 | 5/2005 | Michelson |
| 6,899,735 B2 | 5/2005 | Coates et al. |
| 6,902,580 B2 | 6/2005 | Fallin et al. |
| 6,916,340 B2 | 7/2005 | Metzger et al. |
| 6,923,811 B1 | 8/2005 | Carl et al. |
| 6,923,830 B2 | 8/2005 | Michelson |
| 6,936,071 B1 | 8/2005 | Marnay et al. |
| 6,955,691 B2 | 10/2005 | Chae et al. |
| 6,962,606 B2 | 11/2005 | Michelson |
| 6,964,686 B2 | 11/2005 | Gordon |
| 6,964,687 B1 | 11/2005 | Bernard et al. |
| 6,966,929 B2 | 11/2005 | Mitchell |
| 6,972,019 B2 | 12/2005 | Michelson |
| 6,972,035 B2 | 12/2005 | Michelson |
| 6,981,975 B2 | 1/2006 | Michelson |
| 6,984,234 B2 | 1/2006 | Bray |
| 6,984,245 B2 | 1/2006 | McGahan et al. |
| 6,986,789 B2 | 1/2006 | Schultz et al. |
| 6,994,727 B2 | 2/2006 | Khandkar et al. |
| 7,001,385 B2 | 2/2006 | Bonutti |
| 7,001,432 B2 | 2/2006 | Keller et al. |
| 7,008,453 B1 | 3/2006 | Michelson |

(56) References Cited

U.S. PATENT DOCUMENTS

| | | |
|---|---|---|
| 7,011,684 B2 | 3/2006 | Eckman |
| 7,018,412 B2 | 3/2006 | Ferreira et al. |
| 7,025,787 B2 | 4/2006 | Bryan et al. |
| 7,033,394 B2 | 4/2006 | Michelson |
| 7,041,135 B2 | 5/2006 | Michelson |
| 7,041,136 B2 | 5/2006 | Goble et al. |
| 7,048,762 B1 | 5/2006 | Sander et al. |
| 7,048,765 B1 | 5/2006 | Grooms et al. |
| 7,051,610 B2 | 5/2006 | Stoianovici et al. |
| 7,056,344 B2 | 6/2006 | Huppert et al. |
| 7,060,097 B2 | 6/2006 | Fraser et al. |
| 7,060,099 B2 | 6/2006 | Carli et al. |
| 7,063,701 B2 | 6/2006 | Michelson |
| 7,063,702 B2 | 6/2006 | Michelson |
| 7,066,961 B2 | 6/2006 | Michelson |
| 7,074,237 B2 | 7/2006 | Goble et al. |
| 7,090,698 B2 | 8/2006 | Goble et al. |
| 7,094,239 B1 | 8/2006 | Michelson |
| 7,105,023 B2 | 9/2006 | Eckman |
| 7,105,024 B2 | 9/2006 | Richelsoph |
| 7,112,206 B2 | 9/2006 | Michelson |
| 7,118,579 B2 | 10/2006 | Michelson |
| 7,118,580 B1 | 10/2006 | Beyersdorff et al. |
| 7,118,598 B2 | 10/2006 | Michelson |
| 7,128,760 B2 | 10/2006 | Michelson |
| 7,128,761 B2 | 10/2006 | Kuras et al. |
| 7,137,984 B2 | 11/2006 | Michelson |
| 7,147,665 B1 | 12/2006 | Bryan et al. |
| 7,153,325 B2 | 12/2006 | Kim et al. |
| 7,163,561 B2 | 1/2007 | Michelson |
| 7,169,153 B2 | 1/2007 | Keller |
| 7,175,662 B2 | 2/2007 | Link et al. |
| 7,179,294 B2 | 2/2007 | Eisermann et al. |
| 7,198,644 B2 | 4/2007 | Schultz et al. |
| 7,204,851 B2 | 4/2007 | Trieu et al. |
| 7,204,852 B2 | 4/2007 | Marnay et al. |
| 7,211,112 B2 | 5/2007 | Baynham et al. |
| 7,217,291 B2 | 5/2007 | Zucherman et al. |
| 7,217,292 B2 | 5/2007 | Ralph et al. |
| 7,217,293 B2 | 5/2007 | Branch |
| 7,223,289 B2 | 5/2007 | Trieu et al. |
| 7,232,463 B2 | 6/2007 | Falahee |
| 7,232,464 B2 | 6/2007 | Mathieu |
| 7,235,082 B2 | 6/2007 | Bartish et al. |
| 7,255,698 B2 | 8/2007 | Michelson |
| 7,276,081 B1 | 10/2007 | Coates et al. |
| 7,291,170 B2 | 11/2007 | Huppert |
| 7,303,583 B1 | 12/2007 | Schär et al. |
| 7,326,248 B2 | 2/2008 | Michelson |
| 7,326,250 B2 | 2/2008 | Beaurain et al. |
| 7,361,196 B2 | 4/2008 | Fallin et al. |
| 7,404,795 B2 | 7/2008 | Ralph et al. |
| 7,410,501 B2 | 8/2008 | Michelson |
| 7,419,505 B2 | 9/2008 | Fleischmann et al. |
| 7,431,735 B2 | 10/2008 | Liu et al. |
| 7,435,262 B2 | 10/2008 | Michelson |
| 7,442,209 B2 | 10/2008 | Michelson |
| 7,445,636 B2 | 10/2008 | Liu et al. |
| 7,445,635 B2 | 11/2008 | Fallin et al. |
| 7,455,684 B2 | 11/2008 | Gradel et al. |
| 7,455,692 B2 | 11/2008 | Michelson |
| 7,465,317 B2 | 12/2008 | Malberg et al. |
| 7,473,276 B2 | 1/2009 | Aebi et al. |
| 7,479,160 B2 | 1/2009 | Branch et al. |
| 7,481,840 B2 | 1/2009 | Zucherman et al. |
| 7,494,507 B2 | 2/2009 | Dixon et al. |
| 7,494,508 B2 | 2/2009 | Zeegers |
| 7,503,933 B2 | 3/2009 | Michelson |
| 7,517,363 B2 | 4/2009 | Rogers et al. |
| 7,540,882 B2 | 6/2009 | Michelson |
| 7,563,284 B2 | 7/2009 | Coppes et al. |
| 7,563,286 B2 | 7/2009 | Gerber et al. |
| 7,566,345 B1 | 7/2009 | Fallin et al. |
| 7,575,599 B2 | 8/2009 | Villiers et al. |
| 7,575,600 B2 | 8/2009 | Zucherman et al. |
| 7,588,590 B2 | 9/2009 | Chervitz et al. |
| 7,591,851 B2 | 9/2009 | Winslow et al. |
| 7,594,931 B2 | 9/2009 | Louis et al. |
| 7,594,932 B2 | 9/2009 | Aferzon et al. |
| 7,601,170 B2 | 10/2009 | Winslow et al. |
| 7,604,654 B2 | 10/2009 | Fallin et al. |
| 7,608,107 B2 | 10/2009 | Michelson |
| 7,611,538 B2 * | 11/2009 | Belliard ............... A61F 2/4425 623/17.15 |
| 7,618,453 B2 | 11/2009 | Goble et al. |
| 7,618,455 B2 | 11/2009 | Goble et al. |
| 7,618,456 B2 | 11/2009 | Mathieu et al. |
| 7,621,955 B2 | 11/2009 | Goble et al. |
| 7,621,956 B2 | 11/2009 | Paul et al. |
| 7,621,958 B2 | 11/2009 | Zdeblick et al. |
| 7,625,393 B2 | 12/2009 | Fallin et al. |
| 7,632,282 B2 | 12/2009 | Dinville |
| 7,637,951 B2 | 12/2009 | Michelson |
| 7,637,953 B2 | 12/2009 | Branch et al. |
| 7,637,954 B2 | 12/2009 | Michelson |
| 7,641,690 B2 | 1/2010 | Abdou |
| 7,655,027 B2 | 2/2010 | Michelson |
| 7,658,766 B2 | 2/2010 | Melkent et al. |
| 7,682,396 B2 | 3/2010 | Beaurain et al. |
| 7,695,516 B2 | 4/2010 | Zeegers |
| 7,695,517 B2 | 4/2010 | Benzel et al. |
| 7,708,776 B1 | 5/2010 | Blain et al. |
| 7,717,959 B2 | 5/2010 | William et al. |
| 7,727,280 B2 | 6/2010 | McLuen |
| 7,744,602 B2 | 6/2010 | Teeny et al. |
| 7,749,252 B2 | 7/2010 | Zucherman et al. |
| 7,749,274 B2 | 7/2010 | Razian |
| 7,753,937 B2 | 7/2010 | Chervitz et al. |
| 7,771,473 B2 | 8/2010 | Thramann |
| 7,771,475 B2 | 8/2010 | Michelson |
| 7,771,478 B2 | 8/2010 | Navarro et al. |
| 7,776,090 B2 | 8/2010 | Winslow et al. |
| 7,780,670 B2 | 8/2010 | Bonutti |
| 7,789,914 B2 | 9/2010 | Michelson |
| 7,794,502 B2 | 9/2010 | Michelson |
| 7,799,053 B2 | 9/2010 | Haid, Jr. et al. |
| 7,799,057 B2 | 9/2010 | Hudgins et al. |
| 7,799,081 B2 | 9/2010 | McKinley |
| 7,811,326 B2 | 10/2010 | Braddock, Jr. et al. |
| 7,819,903 B2 | 10/2010 | Fraser et al. |
| 7,824,445 B2 | 11/2010 | Biro et al. |
| 7,833,255 B2 | 11/2010 | Chow et al. |
| 7,842,088 B2 * | 11/2010 | Rashbaum ............ A61F 2/4425 623/17.15 |
| 7,846,188 B2 | 12/2010 | Moskowitz et al. |
| 7,846,207 B2 | 12/2010 | Lechmann et al. |
| 7,850,731 B2 | 12/2010 | Brittan et al. |
| 7,850,732 B2 | 12/2010 | Heinz |
| 7,850,733 B2 | 12/2010 | Baynham et al. |
| 7,862,616 B2 | 1/2011 | Lechmann et al. |
| 7,871,441 B2 | 1/2011 | Eckman |
| 7,875,076 B2 | 1/2011 | Mathieu et al. |
| 7,887,591 B2 | 2/2011 | Aebi et al. |
| 7,892,261 B2 | 2/2011 | Bonutti |
| 7,892,286 B2 | 2/2011 | Michelson |
| 7,896,919 B2 | 3/2011 | Belliard et al. |
| 7,905,886 B1 | 3/2011 | Curran et al. |
| 7,909,871 B2 | 3/2011 | Abdou |
| 7,914,560 B2 | 3/2011 | Hoy et al. |
| 7,922,729 B2 | 4/2011 | Michelson |
| 7,931,674 B2 | 4/2011 | Zucherman et al. |
| 7,931,840 B2 | 4/2011 | Michelson |
| 7,935,149 B2 | 5/2011 | Michelson |
| 7,951,198 B2 | 5/2011 | Sucec et al. |
| 7,955,390 B2 | 6/2011 | Fallin et al. |
| 7,972,337 B2 | 7/2011 | Boyajian et al. |
| 7,972,363 B2 | 7/2011 | Moskowitz et al. |
| 7,972,365 B2 | 7/2011 | Michelson |
| 7,976,566 B2 | 7/2011 | Michelson |
| 7,985,255 B2 | 7/2011 | Bray et al. |
| 7,985,258 B2 | 7/2011 | Zdeblick et al. |
| 7,993,373 B2 | 8/2011 | Hoy et al. |
| 7,998,177 B2 | 8/2011 | Hoy et al. |
| 7,998,178 B2 | 8/2011 | Hoy et al. |

(56) References Cited

U.S. PATENT DOCUMENTS

| | | |
|---|---|---|
| 7,998,211 B2 | 8/2011 | Baccelli et al. |
| 8,002,835 B2 | 8/2011 | Zeegers |
| 8,007,534 B2 | 8/2011 | Michelson |
| 8,021,401 B2 | 9/2011 | Carl et al. |
| 8,021,430 B2 | 9/2011 | Michelson |
| 8,043,334 B2 | 10/2011 | Fisher et al. |
| 8,062,336 B2 | 11/2011 | Triplett et al. |
| 8,062,375 B2 | 11/2011 | Glerum et al. |
| 8,066,741 B2 | 11/2011 | Fallin et al. |
| 8,066,749 B2 | 11/2011 | Winslow et al. |
| 8,070,816 B2 | 12/2011 | Taylor |
| 8,070,819 B2 | 12/2011 | Aferzon et al. |
| 8,075,593 B2 | 12/2011 | Hess |
| 8,075,618 B2 | 12/2011 | Trieu et al. |
| 8,075,621 B2 | 12/2011 | Michelson |
| 8,080,062 B2 | 12/2011 | Armstrong et al. |
| 8,097,034 B2 | 1/2012 | Michelson |
| 8,114,082 B2 | 2/2012 | Boyajian et al. |
| 8,118,873 B2 | 2/2012 | Humphreys et al. |
| 8,137,405 B2 | 3/2012 | Kostuik et al. |
| 8,147,556 B2 | 4/2012 | Louis et al. |
| 8,167,946 B2 | 5/2012 | Michelson |
| 8,167,949 B2 | 5/2012 | Tyber et al. |
| 8,167,950 B2 | 5/2012 | Aferzon et al. |
| 8,182,539 B2 | 5/2012 | Tyber et al. |
| 8,187,329 B2 | 5/2012 | Theofilos |
| 8,187,332 B2 | 5/2012 | Mcluen |
| 8,216,312 B2 | 7/2012 | Gray |
| 8,241,359 B2 | 8/2012 | Davis et al. |
| 8,257,439 B2 | 9/2012 | Zeegers |
| 8,257,443 B2 | 9/2012 | Kamran et al. |
| 8,267,999 B2 | 9/2012 | Beaurain et al. |
| 8,303,663 B2 | 11/2012 | Jimenez et al. |
| 8,313,528 B1 | 11/2012 | Wensel |
| 8,323,345 B2 | 12/2012 | Sledge |
| 8,343,197 B2 | 1/2013 | Gonzalez-Hernandez |
| 8,343,219 B2 | 1/2013 | Allain et al. |
| 8,349,015 B2 | 1/2013 | Bae et al. |
| 8,353,219 B2 | 1/2013 | Brackett et al. |
| 8,388,684 B2 | 3/2013 | Bao et al. |
| 8,439,931 B2 | 5/2013 | Dinville |
| 8,465,546 B2 | 6/2013 | Jodaitis et al. |
| 8,535,352 B2 | 9/2013 | Altarac et al. |
| 8,545,563 B2 | 10/2013 | Brun et al. |
| 8,617,245 B2 | 12/2013 | Brett |
| 8,685,100 B2 | 4/2014 | Jodaitis et al. |
| 8,696,681 B2 | 4/2014 | Harris et al. |
| 8,753,397 B2 | 6/2014 | Beaurain et al. |
| 8,771,284 B2 | 7/2014 | Rashbaum et al. |
| 8,858,635 B2 | 10/2014 | Hovorka et al. |
| 8,974,532 B2 | 3/2015 | Zeegers |
| 8,979,932 B2* | 3/2015 | Rashbaum ............ A61F 2/4425 623/17.14 |
| 9,044,337 B2 | 6/2015 | Dinville et al. |
| 9,597,194 B2* | 3/2017 | Rashbaum ............ A61F 2/4425 |
| 2001/0018614 A1 | 8/2001 | Bianchi |
| 2001/0020185 A1 | 9/2001 | Ray |
| 2001/0031254 A1 | 10/2001 | Bianchi et al. |
| 2001/0031967 A1 | 10/2001 | Nicholson et al. |
| 2002/0016592 A1 | 2/2002 | Branch et al. |
| 2002/0026243 A1 | 2/2002 | Lin |
| 2002/0032483 A1 | 3/2002 | Nicholson et al. |
| 2002/0035400 A1 | 3/2002 | Bryan et al. |
| 2002/0040243 A1 | 4/2002 | Attali et al. |
| 2002/0059938 A1 | 5/2002 | Fogarty et al. |
| 2002/0070565 A1 | 6/2002 | Szapucki et al. |
| 2002/0072806 A1 | 6/2002 | Buskirk et al. |
| 2002/0082597 A1 | 6/2002 | Fraser |
| 2002/0082700 A1 | 6/2002 | Bianchi et al. |
| 2002/0087212 A1 | 7/2002 | James et al. |
| 2002/0106393 A1 | 8/2002 | Bianchi et al. |
| 2002/0107572 A1 | 8/2002 | Foley et al. |
| 2002/0119437 A1 | 8/2002 | Grroms et al. |
| 2002/0138143 A1 | 9/2002 | Grooms et al. |
| 2002/0143343 A1 | 10/2002 | Castro |
| 2002/0151893 A1 | 10/2002 | Santilli |
| 2002/0161375 A1 | 10/2002 | Ralph et al. |
| 2002/0161444 A1 | 10/2002 | Choi |
| 2002/0165612 A1 | 11/2002 | Gerber et al. |
| 2002/0165613 A1 | 11/2002 | Lin et al. |
| 2002/0193880 A1 | 12/2002 | Fraser |
| 2003/0023304 A1 | 1/2003 | Carter et al. |
| 2003/0027125 A1 | 2/2003 | Mills et al. |
| 2003/0028249 A1 | 2/2003 | Baccelli et al. |
| 2003/0055503 A1 | 3/2003 | O'neil |
| 2003/0060886 A1 | 3/2003 | Van Hoeck et al. |
| 2003/0069586 A1 | 4/2003 | Errico et al. |
| 2003/0069640 A1 | 4/2003 | Ferreira et al. |
| 2003/0074075 A1 | 4/2003 | Thomas, Jr. et al. |
| 2003/0093153 A1 | 5/2003 | Banick et al. |
| 2003/0093156 A1 | 5/2003 | Metzger et al. |
| 2003/0097179 A1 | 5/2003 | Carter et al. |
| 2003/0100950 A1 | 5/2003 | Moret |
| 2003/0109928 A1 | 6/2003 | Pasquet et al. |
| 2003/0135279 A1 | 7/2003 | Michelson |
| 2003/0139815 A1 | 7/2003 | Grooms et al. |
| 2003/0149438 A1 | 8/2003 | Nichols et al. |
| 2003/0149484 A1 | 8/2003 | Michelson |
| 2003/0167091 A1 | 9/2003 | Scharf |
| 2003/0171814 A1 | 9/2003 | Muhanna et al. |
| 2003/0187436 A1 | 10/2003 | Bolger et al. |
| 2003/0187506 A1 | 10/2003 | Ross et al. |
| 2003/0191531 A1 | 10/2003 | Berry et al. |
| 2003/0195514 A1 | 10/2003 | Trieu et al. |
| 2003/0195626 A1 | 10/2003 | Huppert |
| 2003/0195629 A1 | 10/2003 | Pafford et al. |
| 2003/0195632 A1 | 10/2003 | Foley et al. |
| 2003/0204260 A1 | 10/2003 | Ferree |
| 2003/0220691 A1 | 11/2003 | Songer et al. |
| 2003/0233145 A1 | 12/2003 | Landry et al. |
| 2003/0233147 A1 | 12/2003 | Nicholson et al. |
| 2004/0002758 A1 | 1/2004 | Landry et al. |
| 2004/0002761 A1 | 1/2004 | Rogers et al. |
| 2004/0010312 A1 | 1/2004 | Enayati |
| 2004/0010316 A1 | 1/2004 | William et al. |
| 2004/0024406 A1 | 2/2004 | Ralph et al. |
| 2004/0030387 A1 | 2/2004 | Landry et al. |
| 2004/0034423 A1 | 2/2004 | Lyons et al. |
| 2004/0073307 A1 | 4/2004 | Keller |
| 2004/0073309 A1 | 4/2004 | Bianchi et al. |
| 2004/0073311 A1 | 4/2004 | Ferree |
| 2004/0073313 A1 | 4/2004 | Link et al. |
| 2004/0083000 A1* | 4/2004 | Keller ............... A61F 2/4425 623/17.14 |
| 2004/0093082 A1 | 5/2004 | Ferree |
| 2004/0093083 A1 | 5/2004 | Branch et al. |
| 2004/0097929 A1 | 5/2004 | Branch et al. |
| 2004/0102846 A1 | 5/2004 | Keller et al. |
| 2004/0111160 A1 | 6/2004 | Evans et al. |
| 2004/0115172 A1 | 6/2004 | Bianchi et al. |
| 2004/0117022 A1 | 6/2004 | Marnay et al. |
| 2004/0127990 A1 | 7/2004 | Bartish, Jr. et al. |
| 2004/0127993 A1 | 7/2004 | Kast et al. |
| 2004/0127994 A1 | 7/2004 | Kast et al. |
| 2004/0133278 A1 | 7/2004 | Marino et al. |
| 2004/0133281 A1 | 7/2004 | Khandkar et al. |
| 2004/0143332 A1 | 7/2004 | Krueger et al. |
| 2004/0148029 A1 | 7/2004 | Bianchi et al. |
| 2004/0153157 A1 | 8/2004 | Keller |
| 2004/0158254 A1 | 8/2004 | Eisermann |
| 2004/0158328 A1 | 8/2004 | Eisermann |
| 2004/0162617 A1 | 8/2004 | Zucherman et al. |
| 2004/0172020 A1 | 9/2004 | Beaurain et al. |
| 2004/0172130 A1 | 9/2004 | Nakahara et al. |
| 2004/0193273 A1 | 9/2004 | Huang |
| 2004/0199254 A1 | 10/2004 | Louis et al. |
| 2004/0210219 A1 | 10/2004 | Bray |
| 2004/0210308 A1 | 10/2004 | Carter et al. |
| 2004/0210313 A1 | 10/2004 | Michelson |
| 2004/0220582 A1 | 11/2004 | Keller |
| 2004/0225295 A1 | 11/2004 | Zubok et al. |
| 2004/0225363 A1 | 11/2004 | Richelsoph |
| 2004/0225364 A1 | 11/2004 | Richelsoph et al. |
| 2004/0230306 A1 | 11/2004 | Hoeck et al. |

(56) References Cited

U.S. PATENT DOCUMENTS

| | | |
|---|---|---|
| 2004/0243238 A1 | 12/2004 | Arnin et al. |
| 2004/0243240 A1 | 12/2004 | Beaurain et al. |
| 2004/0254577 A1 | 12/2004 | Delecrin et al. |
| 2004/0254643 A1 | 12/2004 | Jackson |
| 2005/0004672 A1 | 1/2005 | Pafford et al. |
| 2005/0010215 A1 | 1/2005 | Delecrin et al. |
| 2005/0015094 A1 | 1/2005 | Keller |
| 2005/0015095 A1 | 1/2005 | Keller |
| 2005/0015149 A1 | 1/2005 | Michelson |
| 2005/0021042 A1 | 1/2005 | Marnay et al. |
| 2005/0027359 A1 | 2/2005 | Mashburn |
| 2005/0027360 A1 | 2/2005 | Webb et al. |
| 2005/0027362 A1 | 2/2005 | Williams et al. |
| 2005/0027363 A1 | 2/2005 | Gordon |
| 2005/0033305 A1 | 2/2005 | Schultz |
| 2005/0033428 A1 | 2/2005 | Keller |
| 2005/0033435 A1 | 2/2005 | Belliard et al. |
| 2005/0033437 A1 | 2/2005 | Bao et al. |
| 2005/0033438 A1 | 2/2005 | Schultz et al. |
| 2005/0038511 A1 | 2/2005 | Martz et al. |
| 2005/0038512 A1 | 2/2005 | Michelson |
| 2005/0038516 A1 | 2/2005 | Spoonamore |
| 2005/0043798 A1 | 2/2005 | Eckman |
| 2005/0043800 A1 | 2/2005 | Paul et al. |
| 2005/0043804 A1 | 2/2005 | Gordon et al. |
| 2005/0049590 A1 | 3/2005 | Alleyne et al. |
| 2005/0060034 A1 | 3/2005 | Berry et al. |
| 2005/0060037 A1 | 3/2005 | Michelson |
| 2005/0065608 A1 | 3/2005 | Michelson |
| 2005/0065611 A1 | 3/2005 | Huppert et al. |
| 2005/0071009 A1 | 3/2005 | Muhanna et al. |
| 2005/0085911 A1 | 4/2005 | Link |
| 2005/0085917 A1 | 4/2005 | Marnay et al. |
| 2005/0096742 A1 | 5/2005 | Mills et al. |
| 2005/0096745 A1 | 5/2005 | Andre et al. |
| 2005/0100862 A1 | 5/2005 | Mills et al. |
| 2005/0101957 A1 | 5/2005 | Buskirk et al. |
| 2005/0107788 A1 | 5/2005 | Beaurain et al. |
| 2005/0113926 A1 | 5/2005 | Zucherman et al. |
| 2005/0119665 A1 | 6/2005 | Keller |
| 2005/0119744 A1 | 6/2005 | Buskirk et al. |
| 2005/0119747 A1 | 6/2005 | Fabris Monterumici et al. |
| 2005/0125029 A1 | 6/2005 | Bernard et al. |
| 2005/0131542 A1 | 6/2005 | Benzel et al. |
| 2005/0131544 A1 | 6/2005 | Kuras et al. |
| 2005/0143733 A1 | 6/2005 | Petit |
| 2005/0143824 A1 | 6/2005 | Richelsoph et al. |
| 2005/0143825 A1 | 6/2005 | Enayati |
| 2005/0149189 A1 | 7/2005 | Mokhtar et al. |
| 2005/0154462 A1 | 7/2005 | Zucherman et al. |
| 2005/0159818 A1 | 7/2005 | Blain |
| 2005/0165408 A1 | 7/2005 | Puno et al. |
| 2005/0165483 A1 | 7/2005 | Ray, III et al. |
| 2005/0165485 A1 | 7/2005 | Trieu |
| 2005/0171554 A1 | 8/2005 | Estes et al. |
| 2005/0171610 A1 | 8/2005 | Humphreys et al. |
| 2005/0192671 A1 | 9/2005 | Bao et al. |
| 2005/0197705 A1 | 9/2005 | Arnin et al. |
| 2005/0197706 A1 | 9/2005 | Hovorka et al. |
| 2005/0216086 A1 | 9/2005 | Marik et al. |
| 2005/0216092 A1 | 9/2005 | Marik et al. |
| 2005/0228500 A1 | 10/2005 | Kim et al. |
| 2005/0234553 A1 | 10/2005 | Gordon |
| 2005/0240273 A1 | 10/2005 | Khandkar et al. |
| 2005/0246024 A1 | 11/2005 | Zeegers |
| 2005/0251260 A1 | 11/2005 | Gerber et al. |
| 2005/0256579 A1 | 11/2005 | Keller et al. |
| 2005/0267581 A1 | 12/2005 | Marnay et al. |
| 2005/0273171 A1 | 12/2005 | Gordon et al. |
| 2005/0273173 A1 | 12/2005 | Gordon et al. |
| 2005/0273174 A1 | 12/2005 | Gordon et al. |
| 2005/0273175 A1 | 12/2005 | Gordon et al. |
| 2005/0278026 A1 | 12/2005 | Gordon et al. |
| 2005/0283236 A1 | 12/2005 | Razian |
| 2005/0283242 A1 | 12/2005 | Zucherman et al. |
| 2005/0283244 A1 | 12/2005 | Gordon et al. |
| 2005/0283245 A1 | 12/2005 | Gordon et al. |
| 2005/0283247 A1 | 12/2005 | Gordon et al. |
| 2005/0283248 A1 | 12/2005 | Gordon et al. |
| 2005/0288788 A1 | 12/2005 | Dougherty-shah |
| 2006/0015183 A1 | 1/2006 | Gilbert et al. |
| 2006/0016768 A1 | 1/2006 | Grichar et al. |
| 2006/0020341 A1 | 1/2006 | Schneid et al. |
| 2006/0030860 A1 | 2/2006 | Peterman |
| 2006/0036261 A1 | 2/2006 | Mcdonnell |
| 2006/0036325 A1 | 2/2006 | Paul et al. |
| 2006/0036326 A1 | 2/2006 | Baumgartner et al. |
| 2006/0041313 A1 | 2/2006 | Allard et al. |
| 2006/0041314 A1 | 2/2006 | Millard |
| 2006/0058878 A1 | 3/2006 | Michelson |
| 2006/0069437 A1 | 3/2006 | Weber |
| 2006/0069441 A1* | 3/2006 | Zucherman ............ A61F 2/4425 623/17.15 |
| 2006/0085071 A1 | 4/2006 | Lechmann et al. |
| 2006/0085076 A1 | 4/2006 | Krishna et al. |
| 2006/0085077 A1 | 4/2006 | Cook et al. |
| 2006/0089717 A1 | 4/2006 | Krishna et al. |
| 2006/0095136 A1 | 5/2006 | Mcluen |
| 2006/0111783 A1 | 5/2006 | Aflatoon et al. |
| 2006/0116768 A1 | 6/2006 | Krueger et al. |
| 2006/0116769 A1 | 6/2006 | Marnay et al. |
| 2006/0121084 A1 | 6/2006 | Borden et al. |
| 2006/0122703 A1 | 6/2006 | Aebi et al. |
| 2006/0129244 A1 | 6/2006 | Ensign |
| 2006/0136063 A1* | 6/2006 | Zeegers ............. A61B 17/0642 623/17.14 |
| 2006/0142863 A1 | 6/2006 | Fraser et al. |
| 2006/0149273 A1 | 7/2006 | Ross et al. |
| 2006/0149371 A1 | 7/2006 | Marik et al. |
| 2006/0149378 A1 | 7/2006 | Chase et al. |
| 2006/0155377 A1 | 7/2006 | Beaurain et al. |
| 2006/0155378 A1 | 7/2006 | Eckman |
| 2006/0173544 A1 | 8/2006 | Gau |
| 2006/0178745 A1 | 8/2006 | Bartish, Jr. et al. |
| 2006/0178746 A1 | 8/2006 | Bartish, Jr. et al. |
| 2006/0190082 A1 | 8/2006 | Keller et al. |
| 2006/0200241 A1 | 9/2006 | Rothman et al. |
| 2006/0200242 A1 | 9/2006 | Rothman et al. |
| 2006/0200243 A1 | 9/2006 | Rothman et al. |
| 2006/0206208 A1 | 9/2006 | Michelson |
| 2006/0212123 A1 | 9/2006 | Lechmann et al. |
| 2006/0235426 A1 | 10/2006 | Lim et al. |
| 2006/0235520 A1 | 10/2006 | Pannu |
| 2006/0235526 A1 | 10/2006 | Lemaire |
| 2006/0241621 A1 | 10/2006 | Moskowitz et al. |
| 2006/0241761 A1 | 10/2006 | Gately |
| 2006/0241764 A1 | 10/2006 | Michelson |
| 2006/0253201 A1 | 11/2006 | Mcluen |
| 2006/0259143 A1 | 11/2006 | Navarro et al. |
| 2006/0259147 A1 | 11/2006 | Krishna et al. |
| 2006/0265072 A1 | 11/2006 | Richelsoph |
| 2006/0276899 A1 | 12/2006 | Zipnick et al. |
| 2006/0282074 A1 | 12/2006 | Renaud et al. |
| 2006/0287728 A1 | 12/2006 | Mokhtar et al. |
| 2007/0010886 A1 | 1/2007 | Banick et al. |
| 2007/0010887 A1 | 1/2007 | Williams et al. |
| 2007/0016217 A1 | 1/2007 | Dinville |
| 2007/0016297 A1 | 1/2007 | Johnson |
| 2007/0016299 A1 | 1/2007 | Eckman |
| 2007/0032871 A1 | 2/2007 | Michelson |
| 2007/0049943 A1 | 3/2007 | Moskowitz et al. |
| 2007/0055378 A1 | 3/2007 | Ankney et al. |
| 2007/0073403 A1 | 3/2007 | Lombardo et al. |
| 2007/0073404 A1 | 3/2007 | Rashbaum et al. |
| 2007/0088362 A1 | 4/2007 | Bonutti et al. |
| 2007/0093850 A1 | 4/2007 | Harris et al. |
| 2007/0100454 A1 | 5/2007 | Burgess et al. |
| 2007/0100455 A1 | 5/2007 | Parsons |
| 2007/0100456 A1 | 5/2007 | Dooris et al. |
| 2007/0106388 A1 | 5/2007 | Michelson |
| 2007/0118223 A1 | 5/2007 | Allard et al. |
| 2007/0123985 A1 | 5/2007 | Errico et al. |
| 2007/0142843 A1 | 6/2007 | Dye |
| 2007/0149974 A1 | 6/2007 | Mangione |

(56) References Cited

U.S. PATENT DOCUMENTS

| | | |
|---|---|---|
| 2007/0162128 A1 | 7/2007 | DeRidder et al. |
| 2007/0162130 A1 | 7/2007 | Rashbaum et al. |
| 2007/0162137 A1 | 7/2007 | Kloss et al. |
| 2007/0168040 A1 | 7/2007 | Raymond |
| 2007/0179623 A1 | 8/2007 | Trieu et al. |
| 2007/0208345 A1 | 9/2007 | Marnay et al. |
| 2007/0250167 A1 | 10/2007 | Bray et al. |
| 2007/0250168 A1 | 10/2007 | Lechmann et al. |
| 2007/0260249 A1 | 11/2007 | Boyajian et al. |
| 2007/0270951 A1 | 11/2007 | Davis et al. |
| 2007/0270954 A1 | 11/2007 | Wu |
| 2007/0270960 A1 | 11/2007 | Bonin, Jr. et al. |
| 2007/0270961 A1 | 11/2007 | Ferguson |
| 2007/0270967 A1 | 11/2007 | Fallin et al. |
| 2007/0276498 A1 | 11/2007 | Aebi et al. |
| 2007/0288094 A1 | 12/2007 | Krishna et al. |
| 2007/0293948 A1 | 12/2007 | Bagga et al. |
| 2007/0299524 A1 | 12/2007 | Rivin |
| 2008/0021562 A1 | 1/2008 | Huppert |
| 2008/0027547 A1 | 1/2008 | Yu et al. |
| 2008/0027550 A1 | 1/2008 | Link et al. |
| 2008/0033432 A1 | 2/2008 | Mcgraw et al. |
| 2008/0033555 A1 | 2/2008 | Link et al. |
| 2008/0033562 A1 | 2/2008 | Krishna et al. |
| 2008/0051887 A1 | 2/2008 | Carter et al. |
| 2008/0109083 A1 | 5/2008 | Van Hoeck et al. |
| 2008/0125865 A1 | 5/2008 | Abdelgany |
| 2008/0132949 A1 | 6/2008 | Aferzon et al. |
| 2008/0161930 A1 | 7/2008 | Carls et al. |
| 2008/0161933 A1 | 7/2008 | Grotz et al. |
| 2008/0177306 A1 | 7/2008 | Lamborne et al. |
| 2008/0195211 A1 | 8/2008 | Lin et al. |
| 2008/0200984 A1 | 8/2008 | Jodaitis et al. |
| 2008/0234686 A1 | 9/2008 | Beaurain et al. |
| 2008/0249569 A1 | 10/2008 | Waugh et al. |
| 2008/0249575 A1 | 10/2008 | Waugh et al. |
| 2008/0249625 A1 | 10/2008 | Waugh et al. |
| 2008/0262504 A1 | 10/2008 | Ralph |
| 2008/0281425 A1 | 11/2008 | Thalgott et al. |
| 2008/0294260 A1 | 11/2008 | Gray |
| 2008/0300634 A1 | 12/2008 | Gray |
| 2008/0300685 A1 | 12/2008 | Carls et al. |
| 2008/0306596 A1 | 12/2008 | Jones et al. |
| 2009/0005874 A1 | 1/2009 | Fleischmann et al. |
| 2009/0030461 A1 | 1/2009 | Hoy et al. |
| 2009/0030519 A1 | 1/2009 | Falahee |
| 2009/0030520 A1 | 1/2009 | Biedermann et al. |
| 2009/0076615 A1 | 3/2009 | Duggal et al. |
| 2009/0099601 A1 | 4/2009 | Aferzon et al. |
| 2009/0105830 A1 | 4/2009 | Jones et al. |
| 2009/0105831 A1 | 4/2009 | Jones et al. |
| 2009/0105832 A1 | 4/2009 | Allain et al. |
| 2009/0112271 A1 | 4/2009 | Moskowitz et al. |
| 2009/0118771 A1 | 5/2009 | Gonzalez-Hernandez |
| 2009/0125071 A1 | 5/2009 | Skinlo et al. |
| 2009/0132054 A1 | 5/2009 | Zeegers |
| 2009/0157188 A1 | 6/2009 | Zeegers |
| 2009/0164020 A1 | 6/2009 | Janowski et al. |
| 2009/0182429 A1 | 7/2009 | Humphreys et al. |
| 2009/0182430 A1 | 7/2009 | Tyber et al. |
| 2009/0186333 A1 | 7/2009 | Mills et al. |
| 2009/0192613 A1 | 7/2009 | Wing et al. |
| 2009/0192615 A1 | 7/2009 | Tyber et al. |
| 2009/0204219 A1 | 8/2009 | Beaurain et al. |
| 2009/0210062 A1 | 8/2009 | Thalgott et al. |
| 2009/0216241 A1 | 8/2009 | Dinville |
| 2009/0216331 A1 | 8/2009 | Grotz et al. |
| 2009/0222092 A1 | 9/2009 | Davis et al. |
| 2009/0222100 A1 | 9/2009 | Cipoletti et al. |
| 2009/0228108 A1 | 9/2009 | Keller |
| 2009/0234455 A1 | 9/2009 | Moskowitz et al. |
| 2009/0265007 A1 | 10/2009 | Colleran |
| 2009/0270990 A1 | 10/2009 | Louis et al. |
| 2010/0004664 A1 | 1/2010 | Boyajian et al. |
| 2010/0010547 A1 | 1/2010 | Beaurain et al. |
| 2010/0016903 A1 | 1/2010 | Matityahu et al. |
| 2010/0016974 A1 | 1/2010 | Janowski et al. |
| 2010/0049259 A1 | 2/2010 | Lambrecht et al. |
| 2010/0050276 A1 | 2/2010 | Depaepe |
| 2010/0057206 A1 | 3/2010 | Duffield et al. |
| 2010/0057207 A1 | 3/2010 | Ray, III et al. |
| 2010/0063554 A1 | 3/2010 | Branch et al. |
| 2010/0070037 A1 | 3/2010 | Parry et al. |
| 2010/0070046 A1 | 3/2010 | Steinberg |
| 2010/0082104 A1 | 4/2010 | Carter et al. |
| 2010/0082109 A1 | 4/2010 | Greenhalgh |
| 2010/0087925 A1 | 4/2010 | Kostuik et al. |
| 2010/0106249 A1 | 4/2010 | Tyber et al. |
| 2010/0114317 A1 | 5/2010 | Lambrecht et al. |
| 2010/0121455 A1 | 5/2010 | Lambrecht et al. |
| 2010/0145459 A1 | 6/2010 | Mcdonough et al. |
| 2010/0145460 A1 | 6/2010 | McDonough et al. |
| 2010/0145463 A1 | 6/2010 | Michelson |
| 2010/0152856 A1 | 6/2010 | Overes et al. |
| 2010/0160984 A1 | 6/2010 | Berry et al. |
| 2010/0161057 A1 | 6/2010 | Berry et al. |
| 2010/0179655 A1 | 7/2010 | Hansell et al. |
| 2010/0185289 A1 | 7/2010 | Kirwan et al. |
| 2010/0204796 A1 | 8/2010 | Bae et al. |
| 2010/0211108 A1 | 8/2010 | Lemole, Jr. |
| 2010/0211176 A1 | 8/2010 | Greenhalgh |
| 2010/0217393 A1 | 8/2010 | Theofilos |
| 2010/0217396 A1 | 8/2010 | Bianchi et al. |
| 2010/0234958 A1 | 9/2010 | Linares |
| 2010/0249935 A1 | 9/2010 | Slivka et al. |
| 2010/0249937 A1 | 9/2010 | Blain et al. |
| 2010/0268349 A1 | 10/2010 | Bianchi et al. |
| 2010/0280618 A1 | 11/2010 | Jodaitis et al. |
| 2010/0286777 A1 | 11/2010 | Errico et al. |
| 2010/0286787 A1 | 11/2010 | Villiers et al. |
| 2010/0298941 A1 | 11/2010 | Hes et al. |
| 2010/0305700 A1 | 12/2010 | Ben-arye et al. |
| 2010/0305704 A1 | 12/2010 | Messerli et al. |
| 2010/0312344 A1 | 12/2010 | Reiley |
| 2010/0312345 A1 | 12/2010 | Duffield et al. |
| 2010/0312346 A1 | 12/2010 | Kueenzi et al. |
| 2011/0004310 A1 | 1/2011 | Michelson |
| 2011/0009966 A1 | 1/2011 | Michelson |
| 2011/0015745 A1 | 1/2011 | Bucci |
| 2011/0035007 A1 | 2/2011 | Patel et al. |
| 2011/0040382 A1 | 2/2011 | Muhanna |
| 2011/0054616 A1 | 3/2011 | Kamran et al. |
| 2011/0077738 A1 | 3/2011 | Ciupik et al. |
| 2011/0077739 A1 | 3/2011 | Rashbaum et al. |
| 2011/0082553 A1 | 4/2011 | Abdou |
| 2011/0087327 A1 | 4/2011 | Lechmann et al. |
| 2011/0093077 A1 | 4/2011 | Aebi et al. |
| 2011/0098747 A1 | 4/2011 | Donner et al. |
| 2011/0112587 A1 | 5/2011 | Patel et al. |
| 2011/0118843 A1 | 5/2011 | Mathieu et al. |
| 2011/0125267 A1 | 5/2011 | Michelson |
| 2011/0137420 A1 | 6/2011 | Michelson |
| 2011/0144703 A1 | 6/2011 | Krause et al. |
| 2011/0160860 A1 | 6/2011 | Johnston et al. |
| 2011/0166655 A1 | 7/2011 | Michelson |
| 2011/0166656 A1 | 7/2011 | Thalgott et al. |
| 2011/0166657 A1 | 7/2011 | Thalgott et al. |
| 2011/0166658 A1 | 7/2011 | Garber et al. |
| 2011/0172774 A1 | 7/2011 | Varela |
| 2011/0178599 A1 | 7/2011 | Brett |
| 2011/0196492 A1 | 8/2011 | Lambrecht et al. |
| 2011/0196493 A1 | 8/2011 | Pimenta |
| 2011/0196494 A1 | 8/2011 | Yedlicka et al. |
| 2011/0202136 A1 | 8/2011 | Brittan et al. |
| 2011/0208311 A1 | 8/2011 | Janowski |
| 2011/0208313 A1 | 8/2011 | Michelson |
| 2011/0230969 A1 | 9/2011 | Biedermann et al. |
| 2011/0230971 A1 | 9/2011 | Donner et al. |
| 2011/0264227 A1 | 10/2011 | Boyajian et al. |
| 2011/0295371 A1 | 12/2011 | Moskowitz et al. |
| 2011/0301707 A1 | 12/2011 | Buskirk et al. |
| 2011/0301713 A1 | 12/2011 | Theofilos |
| 2011/0301714 A1 | 12/2011 | Theofilos |
| 2011/0313528 A1 | 12/2011 | Laubert et al. |

(56) References Cited

U.S. PATENT DOCUMENTS

| | | | |
|---|---|---|---|
| 2012/0004660 A1 | 1/2012 | Grooms et al. |
| 2012/0022654 A1 | 1/2012 | Farris et al. |
| 2012/0053693 A1 | 3/2012 | Zeegers |
| 2012/0078371 A1 | 3/2012 | Gamache et al. |
| 2012/0116466 A1 | 5/2012 | Dinville et al. |
| 2012/0191196 A1 | 7/2012 | Louis et al. |
| 2012/0197404 A1 | 8/2012 | Brun et al. |
| 2012/0330424 A1 | 12/2012 | Zeegers |
| 2013/0013006 A1 | 1/2013 | Rashbaum et al. |
| 2013/0150968 A1 | 6/2013 | Dinville et al. |
| 2013/0166029 A1 | 6/2013 | Dinville et al. |
| 2013/0226300 A1 | 8/2013 | Chataigner et al. |
| 2013/0253648 A1 | 9/2013 | Beaurain et al. |
| 2013/0253651 A1 | 9/2013 | Dinville |
| 2013/0282124 A1 | 10/2013 | Jodaitis et al. |
| 2014/0114413 A1 | 4/2014 | Allain et al. |
| 2015/0051702 A1 | 2/2015 | Chataigner et al. |
| 2015/0190240 A1 | 7/2015 | Rashbaum et al. |
| 2016/0008142 A1 | 1/2016 | Louis et al. |

FOREIGN PATENT DOCUMENTS

| | | |
|---|---|---|
| CA | 2533473 C | 3/2011 |
| CA | 2622028 C | 4/2014 |
| DE | 2263842 A1 | 7/1974 |
| DE | 2804936 A1 | 8/1979 |
| DE | 3023353 A1 | 4/1981 |
| DE | 3741493 A1 | 6/1989 |
| DE | 8912648 U1 | 11/1990 |
| DE | 4328690 A1 | 3/1995 |
| DE | 4327054 C1 | 4/1995 |
| DE | 29911422 U1 | 8/1999 |
| DE | 20310432 U1 | 9/2003 |
| DE | 20310433 U1 | 9/2003 |
| DE | 20320454 U1 | 10/2004 |
| DE | 10323363 A1 | 12/2004 |
| DE | 102004027986 A1 | 7/2005 |
| EP | 42271 A1 | 12/1981 |
| EP | 0042271 A1 | 12/1981 |
| EP | 176728 A1 | 4/1986 |
| EP | 0298235 A1 | 1/1989 |
| EP | 0317972 A1 | 5/1989 |
| EP | 0333990 A2 | 9/1989 |
| EP | 0356112 A2 | 2/1990 |
| EP | 0512529 A1 | 11/1992 |
| EP | 0560141 A1 | 9/1993 |
| EP | 0566810 A1 | 10/1993 |
| EP | 0637439 A1 | 2/1995 |
| EP | 0667127 A1 | 8/1995 |
| EP | 0697200 A1 | 2/1996 |
| EP | 0738504 A1 | 10/1996 |
| EP | 0747025 A1 | 12/1996 |
| EP | 0852934 A1 | 7/1998 |
| EP | 0903126 A1 | 3/1999 |
| EP | 0951879 A2 | 10/1999 |
| EP | 0955021 A1 | 11/1999 |
| EP | 0965313 A1 | 12/1999 |
| EP | 0978258 A1 | 2/2000 |
| EP | 1222903 A1 | 7/2002 |
| EP | 1250898 A1 | 10/2002 |
| EP | 1287795 A1 | 3/2003 |
| EP | 1344506 A1 | 9/2003 |
| EP | 1344508 A1 | 9/2003 |
| EP | 1504733 A1 | 2/2005 |
| EP | 1374808 B1 | 12/2005 |
| EP | 2113228 A1 | 11/2009 |
| EP | 2327375 A1 | 6/2011 |
| EP | 2340788 A1 | 7/2011 |
| EP | 2363080 A1 | 9/2011 |
| FR | 2124815 A5 | 9/1972 |
| FR | 2372622 A1 | 6/1978 |
| FR | 2659226 A2 | 9/1991 |
| FR | 2703580 A1 | 10/1994 |
| FR | 2716619 A1 | 9/1995 |
| FR | 2718635 A1 | 10/1995 |
| FR | 2723841 A1 | 3/1996 |
| FR | 2724108 A1 | 3/1996 |
| FR | 2730159 A1 | 8/1996 |
| FR | 2733413 A1 | 10/1996 |
| FR | 2737656 A1 | 2/1997 |
| FR | 2747034 A1 | 10/1997 |
| FR | 2632516 A1 | 12/1999 |
| FR | 2787019 A1 | 6/2000 |
| FR | 2787021 A1 | 6/2000 |
| FR | 2808995 A1 | 11/2001 |
| FR | 2823095 A1 | 10/2002 |
| FR | 2824261 A1 | 11/2002 |
| FR | 2827156 A1 | 1/2003 |
| FR | 2831796 A1 | 5/2003 |
| FR | 2843293 A1 | 2/2004 |
| FR | 2846550 A1 | 5/2004 |
| FR | 2861582 A1 | 5/2005 |
| FR | 2865629 A1 | 8/2005 |
| FR | 2865630 A1 | 8/2005 |
| FR | 2869528 A1 | 11/2005 |
| FR | 2879436 A1 | 6/2006 |
| FR | 2880795 A1 | 7/2006 |
| FR | 2887762 A1 | 1/2007 |
| FR | 2891135 A1 | 3/2007 |
| FR | 2893838 A1 | 6/2007 |
| FR | 2897259 A1 | 8/2007 |
| FR | 2916956 A1 | 12/2008 |
| FR | 2987256 A1 | 8/2013 |
| FR | 3005569 A1 | 11/2014 |
| FR | 3016793 A1 | 7/2015 |
| JP | 2261446 A | 10/1990 |
| RU | 2004218 C1 | 12/1993 |
| WO | WO-9011740 A1 | 10/1990 |
| WO | WO-1991007931 A1 | 6/1991 |
| WO | WO-9113598 A1 | 9/1991 |
| WO | WO-9301771 A1 | 2/1993 |
| WO | WO-9404100 A1 | 3/1994 |
| WO | WO-9508306 A1 | 3/1995 |
| WO | WO-9515133 A1 | 6/1995 |
| WO | WO-9715248 A1 | 5/1997 |
| WO | WO-9801091 A1 | 1/1998 |
| WO | WO-9817209 A2 | 4/1998 |
| WO | WO-9855052 A1 | 12/1998 |
| WO | WO-9909914 A1 | 3/1999 |
| WO | WO-1999053871 A1 | 10/1999 |
| WO | WO-9956675 A1 | 11/1999 |
| WO | WO-9956676 A1 | 11/1999 |
| WO | WO-9963914 A1 | 12/1999 |
| WO | WO-1999065412 A1 | 12/1999 |
| WO | WO-1999066864 A1 | 12/1999 |
| WO | WO-0024327 A2 | 5/2000 |
| WO | WO-0053127 A1 | 9/2000 |
| WO | WO-0074606 A1 | 12/2000 |
| WO | WO-0101893 A1 | 1/2001 |
| WO | WO-0119295 A1 | 3/2001 |
| WO | WO-0143620 A2 | 6/2001 |
| WO | WO-2001041680 A1 | 6/2001 |
| WO | WO-2001062191 A2 | 8/2001 |
| WO | WO-0170141 A1 | 9/2001 |
| WO | WO-0187194 A1 | 11/2001 |
| WO | WO-02013732 A2 | 2/2002 |
| WO | WO-02058599 A2 | 8/2002 |
| WO | WO-2002071960 A1 | 9/2002 |
| WO | WO-02089701 A2 | 11/2002 |
| WO | WO-03005939 A2 | 1/2003 |
| WO | WO-2003015646 A2 | 2/2003 |
| WO | WO-03026522 A2 | 4/2003 |
| WO | WO-03039400 A2 | 5/2003 |
| WO | WO-2003045262 A2 | 6/2003 |
| WO | WO-03059212 A1 | 7/2003 |
| WO | WO-03075804 A1 | 9/2003 |
| WO | WO-2003075803 A1 | 9/2003 |
| WO | WO-03099172 A1 | 12/2003 |
| WO | WO-2004034935 A1 | 4/2004 |
| WO | WO-2004039291 A1 | 5/2004 |
| WO | WO-2004041129 A1 | 5/2004 |
| WO | WO-2004041131 A2 | 5/2004 |
| WO | WO-2004071360 A2 | 8/2004 |
| WO | WO-2004080356 A2 | 9/2004 |

(56) References Cited

FOREIGN PATENT DOCUMENTS

| | | |
|---|---|---|
| WO | WO-2004089256 A1 | 10/2004 |
| WO | WO-2005007040 A1 | 1/2005 |
| WO | WO-2005007044 A1 | 1/2005 |
| WO | WO-2005046534 A1 | 5/2005 |
| WO | WO-2005051243 A2 | 6/2005 |
| WO | WO-2005063150 A1 | 7/2005 |
| WO | WO-2005074839 A1 | 8/2005 |
| WO | WO-05104996 A1 | 11/2005 |
| WO | WO-2005117728 A1 | 12/2005 |
| WO | WO-2006016384 A1 | 2/2006 |
| WO | WO-2006047587 A2 | 5/2006 |
| WO | WO-2006062960 A2 | 6/2006 |
| WO | WO-2006102269 A2 | 9/2006 |
| WO | WO-2006120505 A1 | 11/2006 |
| WO | WO-2006130460 A2 | 12/2006 |
| WO | WO-2006136760 | 12/2006 |
| WO | WO-2007000654 A2 | 1/2007 |
| WO | WO-2007034310 A1 | 3/2007 |
| WO | WO-2007063398 A2 | 6/2007 |
| WO | WO-2007078978 A2 | 7/2007 |
| WO | WO-2007093900 A2 | 8/2007 |
| WO | WO-2008044057 A1 | 4/2008 |
| WO | WO-2008099277 A2 | 8/2008 |
| WO | WO-2008149223 A2 | 12/2008 |
| WO | WO-2009033100 A1 | 3/2009 |
| WO | WO-2010090801 A2 | 8/2010 |
| WO | WO-2011080535 | 7/2011 |
| WO | WO-2011129973 A1 | 10/2011 |
| WO | WO-2013124453 A1 | 8/2013 |
| WO | WO-2014184367 A1 | 11/2014 |
| WO | WO-2015114122 A1 | 8/2015 |

OTHER PUBLICATIONS

"U.S. Appl. No. 10/476,565, Final Office Action dated May 7, 2007", 8 pgs.
"U.S. Appl. No. 10/476,565, Non Final Office Action dated Jul. 18, 2006", 9 pgs.
"U.S. Appl. No. 10/476,565, Notice of Allowance dated Nov. 29, 2007", 4 pgs.
"U.S. Appl. No. 10/476,565, Response filed Jan. 17, 2007 to Non Final Office Action dated Jul. 18, 2006", 23 pgs.
"U.S. Appl. No. 10/476,565, Response filed Nov. 6, 2007 to Final Office Action dated May 7, 2007", 37 pgs.
"U.S. Appl. No. 10/483,563, Corrected Notice of Allowance dated Jun. 19, 2009", 4 pgs.
"U.S. Appl. No. 10/483,563, Final Office Action dated Oct. 28, 2008", 9 pgs.
"U.S. Appl. No. 10/483,563, Non Final Office Action dated Jan. 31, 2008", 8 pgs.
"U.S. Appl. No. 10/483,563, Non Final Office Action dated Feb. 21, 2007", 6 pgs.
"U.S. Appl. No. 10/483,563, Non Final Office Action dated Oct. 30, 2007", 6 pgs.
"U.S. Appl. No. 10/483,563, Notice of Allowance dated Jun. 5, 2009", 4 pgs.
"U.S. Appl. No. 10/483,563, Response filed Apr. 28, 2009 to Final Office Action dated Oct. 28, 2008", 8 pgs.
"U.S. Appl. No. 10/483,563, Response filed Jul. 31, 2008 to Non Final Office Action dated Jan. 31, 2008", 13 pgs.
"U.S. Appl. No. 10/483,563, Response filed Aug. 21, 2007 to Non Final Office Action dated Feb. 21, 2007", 12 pgs.
"U.S. Appl. No. 10/483,563, Response filed Nov. 19, 2007 to Non Final Office Action dated Oct. 30, 2007", 4 pgs.
"U.S. Appl. No. 10/494,418, Notice of Allowance dated Sep. 20, 2005", 12 pgs.
"U.S. Appl. No. 10/533,846, Final Office Action dated Oct. 15, 2008", 13 pgs.
"U.S. Appl. No. 10/533,846, Non Final Office Action dated Apr. 18, 2007", 11 pgs.
"U.S. Appl. No. 10/533,846, Non Final Office Action dated Dec. 26, 2007", 14 pgs.
"U.S. Appl. No. 10/533,846, Notice of Allowance dated Nov. 4, 2009", 4 pgs.
"U.S. Appl. No. 10/533,846, Response filed Apr. 15, 2009 to Final Office Action dated Oct. 15, 2008", 13 pgs.
"U.S. Appl. No. 10/533,846, Response filed Jun. 25, 2008 to Non Final Office Action dated Dec. 26, 2007", 18 pgs.
"U.S. Appl. No. 10/533,846, Response filed Oct. 16, 2007 to Non Final Office Action dated Apr. 18, 2007", 16 pgs.
"U.S. Appl. No. 11/051,710, Appeal Brief filed Jan. 15, 2013", 27 pgs.
"U.S. Appl. No. 11/051,710, Final Office Action dated Jul. 20, 2010", 9 pgs.
"U.S. Appl. No. 11/051,710, Final Office Action dated Dec. 15, 2011", 9 pgs.
"U.S. Appl. No. 11/051,710, Non Final Office Action dated Apr. 11, 2011", 9 pgs.
"U.S. Appl. No. 11/051,710, Non Final Office Action dated Oct. 26, 2009", 12 pgs.
"U.S. Appl. No. 11/051,710, Notice of Allowance dated Apr. 11, 2013", 9 pgs.
"U.S. Appl. No. 11/051,710, Notice of Allowance dated Jun. 11, 2014", 6 pgs.
"U.S. Appl. No. 11/051,710, Response filed Jan. 20, 2011 to Final Office Action dated Jul. 20, 2010", 19 pgs.
"U.S. Appl. No. 11/051,710, Response filed Apr. 26, 2010 to Non Final Office Action dated Oct. 26, 2009", 19 pgs.
"U.S. Appl. No. 11/051,710, Response filed Oct. 11, 2011 to Non Final Office Action dated Apr. 11, 2011", 19 pgs.
"U.S. Appl. No. 11/098,266, Final Office Action dated Aug. 6, 2007", 8 pgs.
"U.S. Appl. No. 11/098,266, Non Final Office Action dated Mar. 22, 2006", 5 pgs.
"U.S. Appl. No. 11/098,266, Non Final Office Action dated Nov. 29, 2006", 5 pgs.
"U.S. Appl. No. 11/098,266, Notice of Allowance dated Apr. 21, 2008", 7 pgs.
"U.S. Appl. No. 11/098,266, Response filed Feb. 6, 2008 to Final Office Action dated Aug. 6, 2007", 14 pgs.
"U.S. Appl. No. 11/098,266, Response filed May 23, 2007 to Non Final Office Action dated Nov. 29, 2006", 10 pgs.
"U.S. Appl. No. 11/098,266, Response filed Aug. 22, 2006 to Non Final Office Action dated Mar. 22, 2006", 17 pgs.
"U.S. Appl. No. 11/109,276, Final Office Action dated Jul. 24, 2008", 12 pgs.
"U.S. Appl. No. 11/109,276, Non Final Office Action dated Feb. 6, 2007", 12 pgs.
"U.S. Appl. No. 11/109,276, Non Final Office Action dated Feb. 13, 2009", 5 pgs.
"U.S. Appl. No. 11/109,276, Non Final Office Action dated Oct. 16, 2007", 12 pgs.
"U.S. Appl. No. 11/109,276, Notice of Allowance dated Dec. 8, 2009", 8 pgs.
"U.S. Appl. No. 11/109,276, Response filed Jan. 26, 2009 to Final Office Action dated Jul. 24, 2008", 9 pgs.
"U.S. Appl. No. 11/109,276, Response filed Apr. 16, 2008 to Non Final Office Action dated Oct. 16, 2007", 16 pgs.
"U.S. Appl. No. 11/109,276, Response filed Aug. 4, 2009 to Non Final Office Action dated Feb. 13, 2009", 8 pgs.
"U.S. Appl. No. 11/109,276, Response filed Aug. 6, 2007 to Non Final Office Action dated Feb. 6, 2007", 39 pgs.
"U.S. Appl. No. 11/180,868, Final Office Action Nov. 5, 2008", 10 pgs.
"U.S. Appl. No. 11/180,868, Non Final Office Action dated Jan. 22, 2008", 15 pgs.
"U.S. Appl. No. 11/180,868, Notice of Allowance dated Jul. 17, 2009", 5 pgs.
"U.S. Appl. No. 11/180,868, Notice of Allowance dated Jul. 31, 2009", 6 pgs.
"U.S. Appl. No. 11/180,868, Response filed May 5, 2009 to Final Office Action dated Nov. 5, 2008", 11 pgs.

(56) References Cited

OTHER PUBLICATIONS

"U.S. Appl. No. 11/180,868, Response filed Jul. 21, 2008 to Non Final Office Action dated Jan. 22, 2008", 15 pgs.
"U.S. Appl. No. 11/341,007, Final Office Action dated Dec. 17, 2009", 17 pgs.
"U.S. Appl. No. 11/341,007, Non Final Office Action dated Apr. 13, 2009", 13 pgs.
"U.S. Appl. No. 11/341,007, Notice of Allowance dated Jul. 26, 2010", 6 pgs.
"U.S. Appl. No. 11/341,007, Response filed Jan. 23, 2009 to Restriction Requirement dated Jul. 23, 2008", 11 pgs.
"U.S. Appl. No. 11/341,007, Response filed Jun. 17, 2010 to Final Office Action dated Dec. 17, 2009", 12 pgs.
"U.S. Appl. No. 11/341,007, Response filed Oct. 13, 2009 to Non Final Office Action dated Apr. 13, 2009", 15 pgs.
"U.S. Appl. No. 11/341,007, Restriction Requirement dated Jul. 23, 2008", 6 pgs.
"U.S. Appl. No. 11/362,253, Amendment and Interview Summary filed Sep. 17, 2015", 11 pgs.
"U.S. Appl. No. 11/362,253, Appeal Brief filed Apr. 9, 2012", 38 pgs.
"U.S. Appl. No. 11/362,253, Appeal Decision dated Jul. 17, 2015", 17 pgs.
"U.S. Appl. No. 11/362,253, Examiner's Answer dated Jun. 20, 2012", 18 pgs.
"U.S. Appl. No. 11/362,253, Final Office Action dated Mar. 8, 2011", 18 pgs.
"U.S. Appl. No. 11/362,253, Final Office Action dated Oct. 15, 2009", 15 pgs.
"U.S. Appl. No. 11/362,253, Non Final Office Action dated Jun. 18, 2010", 17 pgs.
"U.S. Appl. No. 11/362,253, Notice of Allowance dated Oct. 14, 2015", 5 pgs.
"U.S. Appl. No. 11/362,253, Reply Brief filed Aug. 20, 2012", 18 pgs.
"U.S. Appl. No. 11/362,253, Response filed Apr. 15, 2010 to Final Office Action dated Oct. 15, 2009", 24 pgs.
"U.S. Appl. No. 11/362,253, Response filed Aug. 18, 2009 to Office Action dated Feb. 18, 2009", 15 pgs.
"U.S. Appl. No. 11/362,253, Response filed Dec. 20, 2010 to Non Final Office Action dated Jun. 18, 2010", 18 pgs.
"U.S. Appl. No. 11/676,237, Appeal Brief filed Oct. 17, 2011", 41 pgs.
"U.S. Appl. No. 11/676,237, Final Office Action dated Sep. 15, 2010", 12 pgs.
"U.S. Appl. No. 11/676,237, Final Office Action dated Nov. 6, 2012", 6 pgs.
"U.S. Appl. No. 11/676,237, Non Final Office Action Feb. 16, 2012", 13 pgs.
"U.S. Appl. No. 11/676,237, Non Final Office Action dated Mar. 20, 2009", 10 pgs.
"U.S. Appl. No. 11/676,237, Non Final Office Action dated Dec. 18, 2009", 11 pgs.
"U.S. Appl. No. 11/676,237, Notice of Allowance dated Feb. 20, 2013", 5 pgs.
"U.S. Appl. No. 11/676,237, Response filed Feb. 6, 2013 to Final Office Action dated Nov. 6, 2012", 9 pgs.
"U.S. Appl. No. 11/676,237, Response filed Jun. 18, 2010 to Non Final Office Action dated Dec. 18, 2009", 15 pgs.
"U.S. Appl. No. 11/676,237, Response filed Jul. 16, 2012 to Non Final Office Action dated Feb. 16, 2012", 11 pgs.
"U.S. Appl. No. 11/676,237, Response filed Sep. 21, 2009 to Non Final Office Action dated Mar. 20, 2009", 13 pgs.
"U.S. Appl. No. 12/025,677, Final Office Action dated Jun. 29, 2012", 8 pgs.
"U.S. Appl. No. 12/025,677, Final Office Action dated Nov. 7, 2014", 12 pgs.
"U.S. Appl. No. 12/025,677, Non Final Office Action dated Feb. 19, 2014", 11 pgs.
"U.S. Appl. No. 12/025,677, Non Final Office Action dated Jun. 20, 2013", 8 pgs.
"U.S. Appl. No. 12/025,677, Non Final Office Action dated Aug. 12, 2015", 7 pgs.
"U.S. Appl. No. 12/025,677, Non Final Office Action dated Oct. 7, 2011", 9 pgs.
"U.S. Appl. No. 12/025,677, Notice of Allowance dated Jan. 7, 2016", 7 pgs.
"U.S. Appl. No. 12/025,677, Response filed Apr. 9, 2012 to Non Final Office Action dated Oct. 7, 2011", 16 pgs.
"U.S. Appl. No. 12/025,677, Response filed May 6, 2015 to Final Office Action dated Nov. 7, 2014", 16 pgs.
"U.S. Appl. No. 12/025,677, Response filed Aug. 19, 2014 to Non Final Office Action dated Feb. 19, 2014", 23 pgs.
"U.S. Appl. No. 12/025,677, Response filed Nov. 12, 2015 to Non Final Office Action dated Aug. 12, 2015", 10 pgs.
"U.S. Appl. No. 12/025,677, Response filed Dec. 20, 2013 to Non Final Office Action dated Jun. 20, 2013", 21 pgs.
"U.S. Appl. No. 12/025,677, Response filed Dec. 29, 2012 to Final Office Action dated Jun. 29, 2012", 20 pgs.
"U.S. Appl. No. 12/134,884, Non Final Office Action dated Jan. 31, 2012", 7 pgs.
"U.S. Appl. No. 12/134,884, Notice of Allowance dated Nov. 1, 2012", 7 pgs.
"U.S. Appl. No. 12/134,884, Response filed Jul. 31, 2012 to Non Final Office Action dated Jan. 31, 2012", 20 pgs.
"U.S. Appl. No. 12/279,664, Non Final Office Action dated Sep. 14, 2011", 13 pgs.
"U.S. Appl. No. 12/279,664, Notice of Allowance dated Apr. 11, 2012", 11 pgs.
"U.S. Appl. No. 12/279,664, Notice of Allowance dated May 29, 2012", 4 pgs.
"U.S. Appl. No. 12/279,664, Response filed Mar. 14, 2012 to Non Final Office Action dated Sep. 14, 2011", 21 pgs.
"U.S. Appl. No. 12/360,050, Non Final Office Action dated Sep. 6, 2011", 11 pgs.
"U.S. Appl. No. 12/360,050, Non Final Office Action dated Dec. 17, 2010", 14 pgs.
"U.S. Appl. No. 12/360,050, Notice of Allowance dated Mar. 26, 2012", 5 pgs.
"U.S. Appl. No. 12/360,050, Notice of Allowance dated May 18, 2012", 4 pgs.
"U.S. Appl. No. 12/360,050, Notice of Allowance dated Jul. 6, 2012", 5 pgs.
"U.S. Appl. No. 12/360,050, Notice of Allowance dated Aug. 2, 2012", 2 pgs.
"U.S. Appl. No. 12/360,050, Response filed Mar. 6, 2012 to Non Final Office Action dated Sep. 6, 2011", 14 pgs.
"U.S. Appl. No. 12/360,050, Response filed Jun. 16, 2011 to Non Final Office Action dated Dec. 17, 2010", 34 pgs.
"U.S. Appl. No. 12/391,086, Non Final Office Action dated Jul. 29, 2010", 10 pgs.
"U.S. Appl. No. 12/391,086, Notice of Allowance dated Apr. 15, 2011", 6 pgs.
"U.S. Appl. No. 12/391,086, Response filed Jan. 31, 2011 to Non Final Office Action dated Jul. 29, 2010", 16 pgs.
"U.S. Appl. No. 12/424,364, Applicant's Summary of Examiner Interview filed May 22, 2012", 3 pgs.
"U.S. Appl. No. 12/424,364, Non Final Office Action dated Jan. 26, 2012", 10 pgs.
"U.S. Appl. No. 12/424,364, Non Final Office Action dated May 18, 2011", 10 pgs.
"U.S. Appl. No. 12/424,364, Non Final Office Action dated May 23, 2012", 6 pgs.
"U.S. Appl. No. 12/424,364, Notice of Allowance dated Jul. 24, 2012", 5 pgs.
"U.S. Appl. No. 12/424,364, Notice of Allowance dated Aug. 2, 2012", 2 pgs.
"U.S. Appl. No. 12/424,364, Response filed Feb. 27, 2012 to Non Final Office Action dated Jan. 26, 2012", 6 pgs.
"U.S. Appl. No. 12/424,364, Response filed Jul. 6, 2012 to Non Final Office Action dated May 23, 2012", 4 pgs.

(56) References Cited

OTHER PUBLICATIONS

"U.S. Appl. No. 12/424,364, Response filed Nov. 18, 2011 to Non Final Office Action dated May 18, 2011", 13 pgs.
"U.S. Appl. No. 12/430,768, Corrected Notice of Allowance dated Jan. 19, 2012", 2 pgs.
"U.S. Appl. No. 12/430,768, Non Final Office Action dated Jun. 14, 2011", 7 pgs.
"U.S. Appl. No. 12/430,768, Notice of Allowance dated Jan. 11, 2012", 5 pgs.
"U.S. Appl. No. 12/430,768, Response filed Dec. 14, 2011 to Non Final Office Action dated Jun. 14, 2011", 7 pgs.
"U.S. Appl. No. 12/435,955, Final Office Action dated Jul. 23, 2012", 9 pgs.
"U.S. Appl. No. 12/435,955, Non Final Office Action dated Oct. 11, 2011", 8 pgs.
"U.S. Appl. No. 12/435,955, Notice of Allowance dated Jan. 16, 2013", 5 pgs.
"U.S. Appl. No. 12/435,955, Response filed Apr. 11, 2012 to Non Final Office Action dated Oct. 11, 2011", 12 pgs.
"U.S. Appl. No. 12/435,955, Response filed Dec. 24, 2012 to Final Office Action dated Jul. 23, 2012", 13 pgs.
"U.S. Appl. No. 12/527,373, 312 Amendment filed Dec. 2, 2013", Request for Continued Examination, 4 pgs.
"U.S. Appl. No. 12/527,373, Appeal Brief filed Apr. 24, 2013", 15 pgs.
"U.S. Appl. No. 12/527,373, Applicant's Summary of Examiner Interview filed Jan. 31, 2014", 3 pgs.
"U.S. Appl. No. 12/527,373, Final Office Action dated Sep. 24, 2012", 8 pgs.
"U.S. Appl. No. 12/527,373, Non Final Office Action dated Dec. 21, 2011", 7 pgs.
"U.S. Appl. No. 12/527,373, Notice of Allowance dated Aug. 30, 2013", 13 pgs.
"U.S. Appl. No. 12/527,373, Notice of Allowance dated Dec. 24, 2013", 8 pgs.
"U.S. Appl. No. 12/527,373, Response filed Jun. 21, 2012 to Non Final Office Action dated Dec. 21, 2011", 15 pgs.
"U.S. Appl. No. 12/884,664, Examiner Interview Summary dated Dec. 18, 2012", 2 pgs.
"U.S. Appl. No. 12/884,664, Non Final Office Action dated Jan. 15, 2013", 7 pgs.
"U.S. Appl. No. 12/884,664, Notice of Allowance dated Aug. 6, 2013", 9 pgs.
"U.S. Appl. No. 12/884,664, Response filed Apr. 10, 2013 to Non Final Office Action dated Jan. 15, 2013", 16 pgs.
"U.S. Appl. No. 12/884,664, Response filed Oct. 16, 2012 to Restriction Requirement dated Sep. 26, 2012", 15 pgs.
"U.S. Appl. No. 12/884,664, Restriction Requirement dated Sep. 26, 2012", 6 pgs.
"U.S. Appl. No. 12/955,898, Final Office Action dated Jan. 10, 2013", 17 pgs.
"U.S. Appl. No. 12/955,898, Non Final Office Action dated Mar. 3, 2014", 11 pgs.
"U.S. Appl. No. 12/955,898, Non Final Office Action dated Jun. 1, 2012", 27 pgs.
"U.S. Appl. No. 12/955,898, Notice of Allowance dated Jan. 29, 2015", 7 pgs.
"U.S. Appl. No. 12/955,898, Notice of Allowance dated Aug. 8, 2014", 7 pgs.
"U.S. Appl. No. 12/955,898, Response filed Apr. 19, 2012 to Restriction Requirement dated Mar. 19, 2012", 11 pgs.
"U.S. Appl. No. 12/955,898, Response filed Jul. 10, 2013 to Final Office Action dated Jan. 10, 2013", 12 pgs.
"U.S. Appl. No. 12/955,898, Response filed Aug. 4, 2014 to Non Final Office Action dated Mar. 3, 2014", 11 pgs.
"U.S. Appl. No. 12/955,898, Response filed Dec. 3, 2012 to Non Final Office Action dated Jun. 1, 2012", 20 pgs.
"U.S. Appl. No. 12/955,898, Restriction Requirement dated Mar. 19, 2012", 9 pgs.
"U.S. Appl. No. 13/158,761, Examiner Interview Summary dated Aug. 1, 2013", 3 pgs.
"U.S. Appl. No. 13/158,761, Examiner Interview Summary dated Oct. 31, 2012", 3 pgs.
"U.S. Appl. No. 13/158,761, Final Office Action dated Aug. 14, 2013", 11 pgs.
"U.S. Appl. No. 13/158,761, Final Office Action dated Oct. 22, 2014", 12 pgs.
"U.S. Appl. No. 13/158,761, Non Final Office Action dated Feb. 28, 2013", 10 pgs.
"U.S. Appl. No. 13/158,761, Notice of Allowance dated May 12, 2015", 5 pgs.
"U.S. Appl. No. 13/158,761, Notice of Allowance dated Sep. 2, 2015", 5 pgs.
"U.S. Appl. No. 13/158,761, Response filed Apr. 22, 2015 to Final Office Action dated Oct. 22, 2014", 10 pgs.
"U.S. Appl. No. 13/158,761, Response filed Jul. 29, 2013 to Non Final Office Action dated Feb. 28, 2013", 12 pgs.
"U.S. Appl. No. 13/158,761, Response filed Nov. 14, 2013 to Final Office Action dated Aug. 14, 2013", 12 pgs.
"U.S. Appl. No. 13/158,761, Response filed Nov. 19, 2012 to Restriction Requirement dated Oct. 17, 2012", 8 pgs.
"U.S. Appl. No. 13/158,761, Restriction Requirement dated Oct. 17, 2012", 6 pgs.
"U.S. Appl. No. 13/158,761, Supplemental Notice of Allowability dated Sep. 25, 2015", 2 pgs.
"U.S. Appl. No. 13/215,123, Final Office Action dated Nov. 18, 2013", 8 pgs.
"U.S. Appl. No. 13/215,123, Non Final Office Action dated May 24, 2013", 17 pgs.
"U.S. Appl. No. 13/215,123, Non Final Office Action dated Nov. 20, 2012", 7 pgs.
"U.S. Appl. No. 13/215,123, Notice of Allowance dated Jan. 20, 2015", 7 pgs.
"U.S. Appl. No. 13/215,123, Notice of Allowance dated Aug. 29, 2014", 7 pgs.
"U.S. Appl. No. 13/215,123, Response filed Mar. 20, 2013 to Non Final Office Action dated Nov. 20, 2012", 9 pgs.
"U.S. Appl. No. 13/215,123, Response filed May 19, 2014 to Final Office Action dated Nov. 18, 2013", 9 pgs.
"U.S. Appl. No. 13/215,123, Response filed Oct. 24, 2013 to Non Final Office Action dated May 24, 2013", 15 pgs.
"U.S. Appl. No. 13/215,123, Supplemental Amendment filed Nov. 11, 2013", 3 pgs.
"U.S. Appl. No. 13/438,352, Non Final Office Action dated Aug. 14, 2014", 8 pgs.
"U.S. Appl. No. 13/438,352, Notice of Allowance dated Mar. 2, 2015", 7 pgs.
"U.S. Appl. No. 13/438,352, Response filed Jan. 14, 2015 to Non Final Office Action dated Aug. 14, 2014", 10 pgs.
"U.S. Appl. No. 13/520,041, Final Office Action dated Oct. 6, 2014", 10 pgs.
"U.S. Appl. No. 13/520,041, Non Final Office Action dated Mar. 20, 2014", 9 pgs.
"U.S. Appl. No. 13/520,041, Non Final Office Action dated Apr. 10, 2015", 7 pgs.
"U.S. Appl. No. 13/520,041, Notice of Allowance dated Nov. 18, 2015", 5 pgs.
"U.S. Appl. No. 13/520,041, Response filed Mar. 6, 2015 to Final Office Action dated Oct. 6, 2014", 12 pgs.
"U.S. Appl. No. 13/520,041, Response filed Aug. 10, 2015 to Non Final Office Action dated Apr. 10, 2015", 11 pgs.
"U.S. Appl. No. 13/520,041, Response filed Sep. 19, 2014 to Non Final Office Action dated Mar. 20, 2014", 5 pgs.
"U.S. Appl. No. 13/538,078, Non Final Office Action dated May 12, 2014", 12 pgs.
"U.S. Appl. No. 13/538,078, Notice of Allowance dated Oct. 20, 2014", 5 pgs.
"U.S. Appl. No. 13/538,078, Response filed Oct. 14, 2014 to Non Final Office Action dated May 12, 2014", 10 pgs.
"U.S. Appl. No. 13/585,063, Final Office Action dated Nov. 4, 2015", 17 pgs.

(56) References Cited

OTHER PUBLICATIONS

"U.S. Appl. No. 13/585,063, Non Final Office Action dated Feb. 11, 2015", 13 pgs.
"U.S. Appl. No. 13/585,063, Response filed Jan. 6, 2015 to Restriction Requirement dated Nov. 6, 2014", 9 pgs.
"U.S. Appl. No. 13/585,063, Response filed Aug. 11, 2015 to Non Final Office Action dated Feb. 11, 2015", 14 pgs.
"U.S. Appl. No. 13/585,063, Restriction Requirement dated Nov. 6, 2014", 8 pgs.
"U.S. Appl. No. 13/603,043, Final Office Action dated Jul. 24, 2014", 11 pgs.
"U.S. Appl. No. 13/603,043, Non Final Office Action dated Apr. 9, 2013", 13 pgs.
"U.S. Appl. No. 13/603,043, Non Final Office Action dated Nov. 21, 2013", 11 pgs.
"U.S. Appl. No. 13/603,043, Notice of Allowance dated Feb. 10, 2015", 5 pgs.
"U.S. Appl. No. 13/603,043, Response filed May 21, 2014 to Non Final Office Action dated Nov. 21, 2013", 13 pgs.
"U.S. Appl. No. 13/603,043, Response filed Oct. 9, 2013 to Non Final Office Action dated Apr. 9, 2013", 37 pgs.
"U.S. Appl. No. 13/603,043, Response filed Dec. 24, 2014 to Final Office Action dated Jul. 24, 2014", 11 pgs.
"U.S. Appl. No. 13/616,448, Non Final Office Action dated Aug. 22, 2013", 6 pgs.
"U.S. Appl. No. 13/616,448, Notice of Allowance dated Feb. 7, 2014", 5 pgs.
"U.S. Appl. No. 13/616,448, Notice of Allowance dated Apr. 21, 2014", 2 pgs.
"U.S. Appl. No. 13/616,448, Response filed Dec. 23, 2013 to Non Final Office Action dated Aug. 22, 2013", 9 pgs.
"U.S. Appl. No. 13/620,797, Non Final Office Action dated Jul. 5, 2013", 6 pgs.
"U.S. Appl. No. 13/620,797, Notice of Allowance dated Jan. 29, 2014", 5 pgs.
"U.S. Appl. No. 13/620,797, Response filed Nov. 5, 2013 to Non Final Office Action dated Jul. 5, 2013", 9 pgs.
"U.S. Appl. No. 13/732,244, Final Office Action dated Feb. 20, 2015", 9 pgs.
"U.S. Appl. No. 13/732,244, Non Final Office Action dated Sep. 19, 2014", 4 pgs.
"U.S. Appl. No. 13/732,244, Non Final Office Action dated Oct. 20, 2015", 6 pgs.
"U.S. Appl. No. 13/732,244, Response filed Jan. 20, 2015 to Non Final Office Action dated Sep. 19, 2014", 12 pgs.
"U.S. Appl. No. 13/732,244, Response filed Jul. 30, 2014 to Restriction Requirement dated Apr. 30, 2014", 4 pgs.
"U.S. Appl. No. 13/732,244, Response filed Aug. 20, 2015 to Final Office Action dated Feb. 20, 2015", 13 pgs.
"U.S. Appl. No. 13/732,244, Restriction Requirement dated Apr. 30, 2014", 5 pgs.
"U.S. Appl. No. 13/774,547, Notice of Allowance dated Feb. 2, 2015", 5 pgs.
"U.S. Appl. No. 13/774,547, Notice of Allowance dated Jul. 3, 2014", 12 pgs.
"U.S. Appl. No. 13/774,547, Notice of Allowance dated Oct. 16, 2014", 8 pgs.
"U.S. Appl. No. 13/892,933, Final Office Action dated Jul. 28, 2014", 7 pgs.
"U.S. Appl. No. 13/892,933, Non Final Office Action dated Jan. 2, 2014", 6 pgs.
"U.S. Appl. No. 13/892,933, Notice of Allowance dated Feb. 13, 2015", 6 pgs.
"U.S. Appl. No. 13/892,933, Notice of Allowance dated Sep. 14, 2015", 5 pgs.
"U.S. Appl. No. 13/892,933, Response filed Apr. 2, 2014 to Non Final Office Action dated Jan. 2, 2014", 10 pgs.
"U.S. Appl. No. 13/892,933, Response filed Dec. 29, 2014 to Final Office Action dated Jul. 28, 2014", 11 pgs.
"U.S. Appl. No. 13/919,704, Final Office Action dated Jun. 2, 2014", 12 pgs.
"U.S. Appl. No. 13/919,704, Final Office Action dated Dec. 29, 2015", 11 pgs.
"U.S. Appl. No. 13/919,704, Non Final Office Action dated Mar. 13, 2015", 11 pgs.
"U.S. Appl. No. 13/919,704, Non Final Office Action dated Oct. 31, 2013", 10 pgs.
"U.S. Appl. No. 13/919,704, Response filed Jan. 31, 2014 to Non Final Office Action dated Oct. 31, 2013", 15 pgs.
"U.S. Appl. No. 13/919,704, Response filed Sep. 14, 2015 to Non Final Office Action dated Mar. 13, 2015", 11 pgs.
"U.S. Appl. No. 13/919,704, Response filed Dec. 2, 2014 to Final Office Action dated Jun. 2, 2014", 13 pgs.
"U.S. Appl. No. 14/064,434, Non Final Office Action dated May 5, 2014", 7 pgs.
"U.S. Appl. No. 14/064,434, Notice of Allowance dated Sep. 8, 2014", 5 pgs.
"U.S. Appl. No. 14/064,434, Response filed Apr. 14, 2014 to Restriction Requirement dated Jan. 13, 2014", 21 pgs.
"U.S. Appl. No. 14/064,434, Response filed Aug. 27, 2014 to Non Final Office Action dated May 5, 2014", 12 pgs.
"U.S. Appl. No. 14/064,434, Restriction Requirement dated Jan. 13, 2014", 6 pgs.
"U.S. Appl. No. 14/242,177, Non Final Office Action dated Oct. 15, 2015", 9 pgs.
"U.S. Appl. No. 14/242,177, Non Final Office Action dated Dec. 22, 2014", 9 pgs.
"U.S. Appl. No. 14/242,177, Response filed Jan. 15, 2016 to Non Final Office Action dated Oct. 15, 2015", 11 pgs.
"U.S. Appl. No. 14/242,177, Response filed Jun. 22, 2015 to Non Final Office Action dated Dec. 22, 2014", 11 pgs.
"U.S. Appl. No. 14/306,785, Final Office Action dated Jun. 22, 2015", 9 pgs.
"U.S. Appl. No. 14/306,785, Non Final Office Action dated Oct. 22, 2014", 6 pgs.
"U.S. Appl. No. 14/306,785, Notice of Allowance dated Oct. 13, 2015", 6 pgs.
"U.S. Appl. No. 14/306,785, Response filed Apr. 22, 2015 to Non Final Office Action dated Oct. 22, 2014", 9 pgs.
"U.S. Appl. No. 14/306,785, Response filed Sep. 22, 2015 to Final Office Action dated Jun. 22, 2015", 11 pgs.
"U.S. Appl. No. 14/325,317, Non Final Office Action dated Dec. 24, 2014", 7 pgs.
"U.S. Appl. No. 14/325,317, Notice of Allowance dated May 6, 2015", 5 pgs.
"U.S. Appl. No. 14/325,317, Response filed Mar. 24, 2015 to Non Final Office Action dated Dec. 24, 2014", 9 pgs.
"U.S. Appl. No. 14/594,770, Restriction Requirement dated Jul. 1, 2015", 6 pgs.
"U.S. Appl. No. 14/642,696, Non Final Office Action dated Sep. 2, 2015", 9 pgs.
"U.S. Appl. No. 14/642,696, Response filed Dec. 2, 2015 to Non Final Office Action dated Sep. 2, 2015", 15 pgs.
"U.S. Appl. No. 14/659,587, Final Office Action dated Aug. 1, 2016", 8 pgs.
"U.S. Appl. No. 14/659,587, Non Final Office Action dated Jan. 28, 2016", 10 pgs.
"U.S. Appl. No. 14/659,587, Non Final Office Action dated Apr. 16, 2015", 12 pgs.
"U.S. Appl. No. 14/659,587, Notice of Allowance dated Oct. 9, 2015", 6 pgs.
"U.S. Appl. No. 14/659,587, Notice of Allowance dated Nov. 16, 2016", 5 pgs.
"U.S. Appl. No. 14/659,587, Response filed Apr. 28, 2016 to Non Final Office Action dated Jan. 28, 2016", 14 pgs.
"U.S. Appl. No. 14/659,587, Response filed Sep. 16, 2015 to Non Final Office Action dated Apr. 16, 2015", 13 pgs.
"U.S. Appl. No. 14/659,587, Response filed Nov. 1, 2016 to Final Office Action dated Aug. 1, 2016", 10 pgs.
"U.S. Appl. No. 14/721,818, Non Final Office Action dated Sep. 24, 2015", 21 pgs.

(56) References Cited

OTHER PUBLICATIONS

"U.S. Appl. No. 14/721,818, Response filed Dec. 28, 2015 to Non Final Office Action dated Sep. 24, 2015", 15 pgs.
"U.S. Appl. No. 14/726,557, Non Final Office Action dated Dec. 30, 2015", 12 pgs.
"European Application Serial No. 02784881.1, Intention to Grant dated Aug. 26, 2010", 24 pgs.
"European Application Serial No. 02784881.1, Office Action dated Mar. 13, 2009", 2 pgs.
"European Application Serial No. 02784881.1, Office Action dated Aug. 4, 2009", 3 pgs.
"European Application Serial No. 02784881.1, Response filed Jul. 22, 2009 to Office Action dated Mar. 13, 2009", 21 pgs.
"European Application Serial No. 02784881.1, Response filed Oct. 14, 2009 to Office Action dated Aug. 4, 2009", 20 pgs.
"European Application Serial No. 05702425.9, Communication Pursuant to Article 94(3) EPC dated Mar. 2, 2009", 3 pgs.
"European Application Serial No. 05702425.9, Notice of Intention to Grant dated Oct. 22, 2010", 35 pgs.
"European Application Serial No. 05702425.9, Response filed Jul. 22, 2009 to Communication Pursuant to Article 94(3) EPC dated Mar. 2, 2009", 16 pgs.
"European Application Serial No. 05857774.3, Communication Pursuant to Article 94(3) EPC dated Apr. 11, 2011", 4 pgs.
"European Application Serial No. 05857774.3, Communication Pursuant to Article 94(3) EPC dated May 6, 2009", 3 pgs.
"European Application Serial No. 05857774.3, Response filed Oct. 11, 2011 to Communication Pursuant to Article 94(3) EPC dated Apr. 11, 2011", 20 pgs.
"European Application Serial No. 05857774.3, Response filed Nov. 13, 2009 to Communication Pursuant to Article 94(3) EPC dated May 6, 2009", 22 pgs.
"European Application Serial No. 07733892.9, Response filed Nov. 26, 2008 to Communication pursuant to Rules 161(1) and 162 EPC dated Oct. 27, 2008", 16 pgs.
"European Application Serial No. 08762820.2, Amendment filed Jan. 6, 2010", 23 pgs.
"European Application Serial No. 08762820.2, Communication Pursuant to Article 94(3) EPC dated Jan. 17, 2012", 4 pgs.
"European Application Serial No. 08762820.2, Response filed Jul. 27, 2012 to Communication Pursuant to Article 94(3) EPC dated Jan. 17, 2012", 23 pgs.
"European Application Serial No. 09009533.2, Extended European Search Report dated Oct. 6, 2009", 4 pgs.
"European Application Serial No. 09009533.2, Response filed Apr. 26, 2010 to Extended European Search Report dated Oct. 6, 2009", 10 pgs.
"European Application Serial No. 10185004.8, Extended European Search Report dated Apr. 6, 2011", 6 pgs.
"European Application Serial No. 11157596.5, Extended European Search Report dated Jun. 8, 2011", 5 pgs.
"European Application Serial No. 11165170.9, Communication Pursuant to Article 94(3) EPC dated May 15, 2012", 5 pgs.
"European Application Serial No. 11165170.9, Extended European Search Report dated Jul. 21, 2011", 7 pgs.
"European Application Serial No. 11165170.9, Response filed Mar. 6, 2012 to Extended European Search Report dated Jul. 21, 2011", 17 pgs.
"European Application Serial No. 13170071.8, Extended European Search Report dated Oct. 1, 2013", 6 pgs.
"France Application Serial No. 0109381, Search Report dated Apr. 5, 2002", 2 pgs.
"France Application Serial No. 0213833, Preliminary Search Report dated Jul. 10, 2003", 2 pgs.
"France Application Serial No. 0413728, Preliminary Search Report dated Aug. 11, 2005", 2 pgs.
"France Application Serial No. 0509740, Preliminary Search Report dated Jun. 27, 2006", 2 pgs.
"France Application Serial No. 0512133, Preliminary Search Report dated Aug. 4, 2006", 2 pgs.
"France Application Serial No. 0601315, Search Report dated Oct. 11, 2006", 2 pgs.
"France Application Serial No. 0704155, Preliminary Search Report dated Jan. 30, 2008", 3 pgs.
"France Application Serial No. 1251733, Search Report dated Dec. 5, 2012", 2 pgs.
"France Application Serial No. 1354421, Search Report dated Feb. 12, 2014", 5 pgs.
"France Application Serial No. 1450749, Search Report dated Sep. 11, 2014", 2 pgs.
"France Application Serial No. 2730159, Preliminary Search Report dated Sep. 29, 1995", 1 pg.
"France Application Serial No. 2824261, Preliminary Search Report dated Feb. 25, 2002", 4 pgs.
"France Application Serial No. 2831796, Preliminary Search Report dated Aug. 2, 2002", 2 pgs.
"France Application Serial No. 2865629, Preliminary Search Report dated Sep. 14, 2004", 2 pgs.
"France Application Serial No. 2865630, Preliminary Search Report dated Jan. 12, 2005", 2 pgs.
"France Application Serial No. 2869528, Preliminary Search Report dated Dec. 13, 2004", 3 pgs.
"France Application Serial No. 9404832, Preliminary Search Report dated Jan. 16, 1995", 1 pg.
"French Application Serial No. 0506652, Preliminary Search Report dated Dec. 21, 2005", 2 pgs.
"International Application Serial No. PCT/EP2013/053622, International Preliminary Report on Patentability dated Jul. 11, 2014", 4 pgs.
"International Application Serial No. PCT/EP2013/053622, International Search Report dated May 29, 2013", 3 pgs.
"International Application Serial No. PCT/EP2013/053622, Written Opinion dated May 29, 2013", 3 pgs.
"International Application Serial No. PCT/EP2014/060135, International Search Report dated Aug. 26, 2014", 7 pgs.
"International Application Serial No. PCT/EP2015/052019, International Search Report dated May 13, 2015", 4 pgs.
"International Application Serial No. PCT/EP2015/052019, Written Opinion dated May 13, 2015", 9 pgs.
"International Application Serial No. PCT/IB2002/002998, International Preliminary Examination Report dated Dec. 22, 2003", 8 pgs.
"International Application Serial No. PCT/IB2002/002998, International Search Report dated Sep. 16, 2003", 6 pgs.
"International Application Serial No. PCT/IB2002/003390, International Preliminary Examination Report dated Nov. 6, 2003", 4 pgs.
"International Application Serial No. PCT/IB2002/003390, International Search Report dated Mar. 3, 2003", 2 pgs.
"International Application Serial No. PCT/IB2002/004642, International Preliminary Examination Report dated Apr. 1, 2004", 4 pgs.
"International Application Serial No. PCT/IB2002/004642, International Search Report dated Jul. 2, 2003", 2 pgs.
"International Application Serial No. PCT/IB2003/004872, International Preliminary Examination Report dated Mar. 1, 2005", 6 pgs.
"International Application Serial No. PCT/IB2003/004872, International Search Report dated Mar. 3, 2004", 3 pgs.
"International Application Serial No. PCT/IB2005/000280, International Preliminary Report on Patentability dated Jan. 16, 2006", 8 pgs.
"International Application Serial No. PCT/IB2005/000280, International Search Report dated Jun. 24, 2005", 5 pgs.
"International Application Serial No. PCT/IB2005/000280, Written Opinion dated Jun. 24, 2005", 8 pgs.
"International Application Serial No. PCT/IB2005/001151, International Preliminary Report on Patentability dated Jun. 28, 2006", 5 pgs.
"International Application Serial No. PCT/IB2005/001151, International Search Report dated Sep. 12, 2005", 3 pgs.
"International Application Serial No. PCT/IB2005/001151, Written Opinion dated Sep. 12, 2005", 5 pgs.

(56) References Cited

OTHER PUBLICATIONS

"International Application Serial No. PCT/IB2005/004093, International Preliminary Report on Patentability dated Feb. 22, 2007", 8 pgs.
"International Application Serial No. PCT/IB2005/004093, International Search Report dated Aug. 31, 2006", 3 pgs.
"International Application Serial No. PCT/IB2005/004093, Written Opinion dated Aug. 31, 2006", 5 pgs.
"International Application Serial No. PCT/IB2006/001781, International Preliminary Report on Patentability dated Jul. 19, 2007", 6 pgs.
"International Application Serial No. PCT/IB2006/001781, International Search Report dated Mar. 22, 2007", 3 pgs.
"International Application Serial No. PCT/IB2006/001781, Written Opinion dated Mar. 22, 2007", 6 pgs.
"International Application Serial No. PCT/IB2006/002632, International Preliminary Report on Patentability dated Aug. 14, 2007", 5 pgs.
"International Application Serial No. PCT/IB2006/002632, International Search Report dated Feb. 23, 2007", 3 pgs.
"International Application Serial No. PCT/IB2006/002632, Written Opinion dated Feb. 23, 2007", 5 pgs.
"International Application Serial No. PCT/IB2006/003418, International Preliminary Report on Patentability dated Nov. 12, 2007", 8 pgs.
"International Application Serial No. PCT/IB2006/003418, International Search Report dated Jul. 24, 2007", 6 pgs.
"International Application Serial No. PCT/IB2006/003418, Written Opinion dated Jul. 24, 2007", 8 pgs.
"International Application Serial No. PCT/IB2007/000367, International Preliminary Report on Patentability dated Feb. 5, 2008", 9 pgs.
"International Application Serial No. PCT/IB2007/000367, International Search Report dated Oct. 22, 2007", 5 pgs.
"International Application Serial No. PCT/IB2007/000367, Written Opinion dated Oct. 22, 2007", 9 pgs.
"International Application Serial No. PCT/IB2008/000349, International Preliminary Report on Patentability dated May 29, 2009", 10 pgs.
"International Application Serial No. PCT/IB2008/000349, International Search Report dated Jan. 12, 2009", 7 pgs.
"International Application Serial No. PCT/IB2008/000349, Written Opinion dated Jan. 12, 2009", 10 pgs.
"International Application Serial No. PCT/IB2008/001484, Amendment filed May 13, 2009", 33 pgs.
"International Application Serial No. PCT/IB2008/001484, International Preliminary Report on Patentability dated Aug. 5, 2009", 6 pgs.
"International Application Serial No. PCT/IB2008/001484, International Search Report dated Feb. 16, 2009", 5 pgs.
"International Application Serial No. PCT/IB2008/001484, Written Opinion dated Feb. 16, 2009", 8 pgs.
"International Application Serial No. PCT/IB2009/008048, Amendment filed Apr. 2, 2012", 24 pgs.
"International Application Serial No. PCT/IB2009/008048, International Preliminary Report on Patentability dated Apr. 18, 2012", 20 pgs.
"International Application Serial No. PCT/IB2009/008048, International Search Report dated Feb. 2, 2011", 6 pgs.
"International Application Serial No. PCT/IB2009/008048, Written Opinion dated Feb. 2, 2011", 15 pgs.
"LDR Medical, by its attorneys; Chapter II amendments for PCT Pub'n. No. WO2006120505", App. No. PCT/IB2005/004093; Oct. 30, 2006; WIPO, 14 pgs.
"LDR Medical, by its attorneys; Terminal Disclaimer in Application Serial No. 13215123 Mar. 20, 2013", 2 pgs.
"Mc+ Le choix de l'ancrage", LDR Medical, (Sep. 19, 2004), 1 pg.
"Mobidisc (Website)", [Online] Retrieved from the internet: <www.ldrmedical.fr/mobidisc.htm>, (Sep. 19, 2004), 1 pg.
"Reply to Office Action in U.S. Appl. No. 13/774,547, filed Feb. 2, 2015", USPTO; Alexandria, Virgina, 6 pgs.
"Request for Continued Examination in U.S. Appl. No. 11/051,710, filed Jul. 11, 2013", LDR Medical, by its attorneys; USPTO; Alexandria, Virgina, 3 pgs.
"USPTO OA dated Feb. 18, 2009 in U.S. Appl. No. 11/632,253", 14 pgs.
Bouduk, N, et al., "A biological basis for instantaneous centres of rotation of the vertebral column", Proc institution Mechanical Engineers, (Jun. 16, 1995), 177-183.
Gertzban, S D, et al., "Centrode Patterns and Segmental Instability in Degenerative Disc Disease", BSc, M. Tile, MD, BSc, {MED), FRCS©, and B. Cruickshank, MD, FRCPath, Spine, vol. 10, No. 3 (Jan. 21, 1984), 257-261.
Griffith, S L, et al., "A Multicenter Retrospective Study of the Clinical Results of the LINK SB Charite Intervertebral Prosthesis", vol. 19, No. 16, (Mar. 21, 1994), 1842-1849.
Haher, T R, et al., "Instantaneous Axis of Rotation as a Function of the Three Columns of the Spine", MS, Spine, vol. 17, No. 6, (Jan. 9, 1992), S149-S154.
Haher, T R, et al., "The Effect of the Three Columns of the Spine on the Instantaneous Axis of Rotation in Flexion and Extension", Spine, vol. 16, No. 8, (Apr. 16, 1991), S312-S318.
Klein, J A, et al., "Relocation of the Bending Axis During Flexion-Extension of Lumbar Intervertebral Discs and its Implications for Prolapse", Spine, vol. 8, No. 6, (Nov. 18, 1982), 659-664.
Kostuik, J P, "Alternatives to Spinal Fusion", vol. 29, No. 4, (Oct. 4, 1998), 701-715.
Liu, X, et al., "A New Technique for the Three-Dimensional Study of the Spine in Vitro and In Vivo by Using a Motion-Analysis System", Journal of Spinal Disorders, vol. 10, No. 4, (Jan. 30, 1997), 329-338.
Pearcy, M J, et al., "Instantaneous Axis of Rotation of the Lumbar Intervertebral Joints", vol. 13, No. 9, (Nov. 15, 1987), 1033-1041.
Seligman, S D, "Computer Analysis of Spinal Segment Motion in Degenerative Disc Disease with and Without Axial Loading", Spine, vol. 9., No. 6, (Dec. 31, 1983), 566-573.
White Ill, A A, et al., "Clinical Biomechanics of the Spine", 2nd Edition, J.B. Lippincott Co., (1990), 128-130.
Yoshioka, T, et al., "Motion Characteristics of the Normal Lumbar Spine in Young Adults: Instantaneous of Axis of Rotation and Vertebral Center Motion Analysis", Journal of Spinal Disorders, vol. 3, No. 2, (1990), 103-113.
"Canadian Application Serial No. 2,622,028, Office Action dated Aug. 2, 2012", 2 pgs.
"Canadian Application Serial No. 2,622,028, Response filed Jan. 31, 2013 to Office Action dated Aug. 2, 2012", 28 pgs.
"Canadian Application Serial No. 2,622,028, Voluntary Amendment filed Jun. 17, 2008", 5 pgs.

\* cited by examiner

INTERVERTEBRAL DISC PROSTHESIS

CROSS REFERENCE TO RELATED APPLICATIONS

This application is a continuation of U.S. application Ser. No. 14/659,587 filed Mar. 16, 2015, and issuing as U.S. Pat. No. 9,597,194 on Mar. 21, 2017, which is a continuation of U.S. application Ser. No. 12/955,898 filed Nov. 29, 2010, and issuing as U.S. Pat. No. 8,989,932 on Mar. 17, 2015, which is a continuation of U.S. application Ser. No. 11/341,007 filed Jan. 27, 2006, and issuing as U.S. Pat. No. 7,842,008 on Nov. 30, 2010, which claims priority from Application No. FR 0509740 filed in France on Sep. 23, 2005, all of which are incorporated herein by reference.

BACKGROUND

The invention relates to an intervertebral disc prosthesis, intended to be substituted for fibrocartilaginous discs providing the liaison between the vertebrae of the spinal column.

Different types of intervertebral disc prostheses are known in the prior art. Numerous prostheses, such as for example those described in the applications WO 02 089 701 and WO 2004/041129, are constituted of a lower plate and an upper plate creating a cage articulated about a central core. Other prostheses like those disclosed in the U.S. Pat. No. 5,676,701 and in the application WO 03/059212 A1, for example, only comprise a lower plate and an upper plate articulated about themselves by means of a surface of articulation. These articulated prostheses have the advantage of offering the patient bearing the prosthesis a freedom of movement, by allowing the plates to tilt and/or rotate in relation to each other. The prostheses comprising a central core, movable between the plates, have the added advantage of allowing a spontaneous positioning of the core in the ideal position for absorbing the constraints imposed on the prosthesis. In these prostheses known in the prior art, the anterior, posterior and lateral edges of a plate are located on the same vertical axis as the corresponding edge of the other plate. This shape of the prosthesis is normally due to the plates being of identical size and that their respective axes of articulation are joined (coaxially), so as to facilitate the movements of the patient and to allow the correction of possible positioning defects. However, these prostheses have the inconvenience of not being perfectly suited to the morphology of the spinal column. Indeed, the posterior edges of two adjacent vertebrae are often slightly off-set to each other. Thus, the prostheses known in the prior art are difficult to properly implant. Additionally, at rest, due to the natural off-setting of the vertebrae and the anchoring of the plates in the vertebrae, the different parts of the prosthesis are under constraint in an undesirable position as it restricts freedom of movement of these parts of the prosthesis. This inconvenience will be diminished through the use of a movable core between the plates, but the possible movements of the core will be restricted and its capacity to position itself so as to absorb the constraints imposed on the prosthesis will therefore be diminished.

In this context, it is beneficial to propose a prosthesis that allows a more efficiently fit to the profile of the spinal column and thus fully attain the goals it set by offering a surface of articulation.

SUMMARY

The purpose of the invention is to overcome some of the inconveniences of the prior art by proposing an intervertebral disc prosthesis at least comprising two plates each bearing at least an edge off-set in relation to the same edge of the other plate.

This goal is reached with an intervertebral disc prosthesis comprising at least two plates, namely first and second plates, articulated about each other by means of a curved surface, namely articulation, of at least one of the plates, allowing to pivot and/or tilt the plates in relation to each other, via rotation about, respectively, an axis substantially perpendicular to the plane of the plates and an axis substantially in the plane of the plates, each of the plates comprising a surface known as a contact surface, intended to be in contact with a vertebral plate of one of the vertebrae between which the prosthesis is intended to be implanted, this contact surface for each of the plates comprising a geometric centre at equal distance from at least two diametrically opposite points located on the periphery of the plate, characterised in that the geometric centres of the plates are not vertically aligned, this off-set of the geometrical centres of the plates engendering an off-set of the edges of the plates in at least one direction perpendicular to the vertical axis of the spinal column.

According to another feature, the second plate comprises a curved surface of articulation of which at least one part co-operates with a curved surface of articulation of the first plate for which it is complementary, in order to allow the articulation, by pivoting and/or tilting, of the plates in relation to each other, the prosthesis comprising a centre of articulation vertically aligned with the vertex of the curved surface of articulation of the second plate and corresponding to the mid-position of the centre of the curved surface of the first plate in relation to the second plate.

According to another feature, the curved surface of the first plate is concave and the curved surface of articulation of the second plate is convex.

According to another feature, the curved surface of the first plate is convex and the curved surface of articulation of the second plate is concave.

According to another feature, the prosthesis also comprises a core comprising a plane surface and a curved surface of articulation and in that only the first plate comprises a curved surface of articulation co-operating with at least one part of the curved surface of the core for which it is complementary, in order to allow the pivoting and/or tilting of the plates in relation to each other, the plane surface of the core co-operating with at least one part of a plane surface of the second plate in order to allow a translation and/or a rotation of the core in relation to the second plate in at least one direction perpendicular to the vertical axis of the spinal column, the second plate comprising means for co-operating complementary with means for co-operating of the core allowing to restrict or abolish at least this translation of the core in relation to the second plate, the prosthesis comprising a centre of articulation vertically aligned with the vertex of the curved surface of articulation of the core and corresponding to the mid-position of the core between the means for co-operating of the second plate and to the mid-position of the centre of the curved surface of the first plate in relation to the core.

According to another feature, the curved surface of the first plate is concave and the curved surface of the core is convex.

According to another feature, the curved surface of the first plate is convex and the curved surface of the core is concave.

According to another feature, the prostheses comprises a centre of articulation vertically aligned with the vertex of the curved surface of articulation, said centre of articulation being vertically aligned with the geometric centre of the first plate but off-set in relation to the geometric centre of the second plate in at least one direction perpendicular to the vertical axis of the spinal column, this off-setting of the geometric centres of the plates engendering an off-setting of the edges of the plates in at least one direction perpendicular to the vertical axis of the spinal column.

According to another feature, the prostheses comprises a centre of articulation vertically aligned with the vertex of the curved surface of articulation, said centre of articulation being off-set in relation to the geometric centre of the first plate but in the opposite direction to that of its off-setting in relation to the geometric centre of the second plate, so that the vertical projection of the centre of articulation is located between the vertical projections of the geometric centres of the plates and that the off-setting of the geometric centres in relation to the centre of articulation cumulate and engender an off-setting of the edges of the plates in at least one direction perpendicular to the vertical axis of the spinal column.

According to another feature, the prostheses comprises a centre of articulation vertically aligned with the vertex of the curved surface of articulation, said centre of articulation being off-set in relation to the geometric centre of the first plate, in the same direction as that of its off-setting in relation to the geometric centre of the second plate, but at a lesser distance so that these off-settings partially compensate each other and engender an off-setting of the edges of the plates between themselves in at least one direction perpendicular to the vertical axis of the spinal column.

According to another feature, the means for co-operating of the second plate are female means located in the vicinity of the edges of the second plate and co-operating with the male means of the core.

According to another feature, the dimensions of each male means for co-operating are slightly smaller than those of the female means for co-operating in order to allow a slight travel between the core and the second plate around the position corresponding to the vertical projection of the centre of articulation.

According to another feature, the dimensions of each male means for co-operating are substantially the same as those of each female means for co-operating in order to prevent any travel between the core and the second plate and to maintain the core in the position corresponding to the vertical projection of the centre of articulation.

According to another feature, the means for co-operating of the second plate are the male means located in the vicinity of the edges of the second plate and co-operating with the female means of the core.

According to another feature, the dimensions of each male means for co-operating are slightly smaller than those of each female means for co-operating in order to allow as slight travel between the core and the second plate, around the position corresponding to the vertical projection of the centre of articulation.

According to another feature, the dimensions of each male means for co-operating are substantially the same as those of each female means for co-operating in order to prevent any travel between the core and the second plate and to maintain the core in the position corresponding to the vertical projection of the centre of articulation.

According to another feature, the male means for co-operating of the core are two studs located on the two side edges of the core and the female means for co-operating of the second plate are four walls located, in pairs, on each of the two side edges of the second plate.

According to another feature, the female means for co-operating of the second plate comprise a section dish-shaped towards the centre of the plate and partly covering the male means for co-operating of the core in order to prevent the core from lifting.

According to another feature, the median planes representing the contact surfaces of the plates are substantially parallel or create an acute angle, the slope obtained by such an angle allowing to adapt the overall shape of the prosthesis to the anatomy of the spinal column or to possibly correct any slope defects of the vertebrae of the patient for whom the prosthesis is intended for.

According to another feature, the plates comprise, at least on their lower edge, at least a bevel facilitating the insertion of the prosthesis between the vertebrae.

According to another feature, the same plates can be assembled with cores of different thicknesses and/or dimensions and/or shapes.

According to another feature, the plates comprise mobile osseous anchorage means.

According to another feature, the osseous anchorage means and/or the plates comprise means for securing the binding of the osseous anchorage means on the plates.

According to another feature, the mobile osseous anchorage means of the plates consists in at least one plate equipped with notches oriented so as to prevent this notched plate from falling out once inserted in a vertebra, one end of the plate having an inward curving section and intended to be interlocked onto at least one edge of an opening located in the vicinity of the periphery of the plates.

According to another feature, the end of the notched plate, opposite the one with an inward curving section, comprises a bevel facilitating the insertion of the notched plate into the vertebrae.

According to another feature, the opening located in the vicinity of the periphery of the plates comprises a sloping section on which the notched plate leans when the curved section of the osseous anchorage means is interlocked onto the edge of this opening, this sloping section thus allowing to set the angle of the osseous anchorage means in relation to the plates and to guide them when being inserted into the opening.

According to another feature, the means for securing consist in flexible tabs oriented towards the curved section of the osseous anchorage means and intended to fold back against the edges of the plate when inserting the osseous anchorage means into the openings in the plates, then to spring back so as to lean against the limit stops located on the walls of the openings in the plates during the interlocking of the curved sections onto the edges of the openings in the plates, so as to prevent the osseous anchorage means from falling out.

According to another feature, the inward curving section of the notched plate of the mobile osseous anchorage means extends by means of a second plate also equipped with notches oriented so as to prevent the plate from falling out once inserted into the vertebra.

According to another feature, the mobile osseous anchorage means of the plates consist in at least a winglet equipped with notches oriented so as to prevent the winglet from falling out once inserted in a groove made in a vertebra, one end of the winglet having an inward curving section and intended to be interlocked on to at least one edge of an opening in the vicinity of the periphery of the plates.

According to another feature, the means for securing the winglet consist in at least one stud located on the lower surface of the winglet and intended to be interlocked into at least one hole in the contact surfaces of the plates, the stud and the hole being of complementary shape and size so as to secure the winglet in place on the plates.

BRIEF DESCRIPTION OF THE DRAWINGS

Other features and advantages of the invention will become clearer upon reading the following description, given in reference to the annexed figures, in which.

DETAILED DESCRIPTION OF THE EMBODIMENTS

Figure 1A:
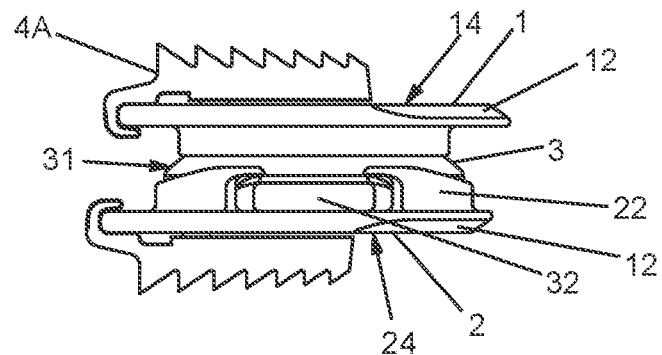
FIGS. 1A, 1B and 1C respectively represent a side view, a rear view with a cross section plane 1C-1C and a cross section along said plane 1C-1C, of an intervertebral disc prosthesis according to an embodiment of the invention, FIGS. 2A, 2B and 2C respectively represent a side view, a rear view with a cross section plane 2C-2C and a cross section along said plane 2C-2C, of an intervertebral disc prosthesis according to another embodiment of the invention, FIGS. 3A and 3B respectively represent a rear view with a cross section plane 3B-3B and a cross section along said plane 3B-3B, of an intervertebral disc prosthesis according to an embodiment of the invention and FIGS. 3C and 3D respectively represent a rear view with a cross section plane 3D-3D and a cross section along said plane 3D-3D, of an intervertebral disc prosthesis according to another embodiment of the invention, FIGS. 4A and 4B respectively represent a top view and a perspective view of an embodiment of the osseous anchorage means of an intervertebral disc prosthesis according to the invention, and FIGS. 4C and 4D respectively represent a top view and a side view of another embodiment of the osseous anchorage means of an intervertebral disc prosthesis according to the invention, FIGS. 5A, 5B and 5C respectively represent a perspective view, a top view and a side view of an intervertebral disc prosthesis according to different embodiments of the invention.

The invention relates to an intervertebral disc prosthesis comprising at least two plates (1, 2) off-set in relation to each other so as to more efficiently follow the anatomy of the spinal column. As explained in the preamble of this application, the vertebrae are generally slightly off-set to each other, so that their edges, for example posterior, are not vertically aligned. The prosthesis according to the invention is thus designed so that the edges of the plates (1, 2) are not vertically aligned and have a slight off-setting corresponding to an off-setting between the edges of the vertebrae between which the prosthesis is intended to be inserted. The off-setting of the vertebrae could have been accurately measured beforehand, in order to choose a prosthesis whose off-setting of the plates (1, 2) perfectly corresponds to the off-setting of the vertebrae.

The plates (1 and 2) of the prosthesis according to the invention each comprise a geometric centre (G1 and G2, respectively) which can be defined, generally speaking, by a point at equal distance from two diametrically opposite points located on the periphery of the plates (1, 2). Normally, the plates of the intervertebral disc prostheses have a relatively straightforward shape and their geometric centre can be of equal distance from all the points located on the periphery of the plates. Irrespective of the prosthesis, a geometric centre can be defined by a point or a surface located at equal distance from the edges of the plate. The geometric centres (G1, G2) of the plates (1, 2) of the prosthesis according to the invention are not vertically aligned but are off-set to each other in at least one direction, for example antero-posterior, perpendicular to the vertical axis of the spinal column. The two plates (1 and 2) of a single intervertebral disc prosthesis are usually substantially the same size and this off-set (D) of the geometric centres (G1, G2) of the plates engenders an off-set of the edges of the plates (1, 2). In the case of a prosthesis whose plates are not of the same size, it is envisaged to off-set the edges of the plates (1 and 2) and the geometric centres (G1, G2) will be even more off-set to each other.

In the different embodiments described below, the prosthesis comprises at least two plates (1 and 2), namely first (1) and second (2) plates, articulated about each other by means of a curved surface (11, 31), namely articulation, of at least one of the plates. This curved surface (11, 31) of articulation allows to pivot the plates (1, 2) about each other, via rotation about an axis substantially perpendicular to the plane of the plates and/or to tilt the plates (1, 2) about each other, via rotation about an axis substantially along the plane of the plates (1, 2). Each of the plates (1, 2) comprises a surface (14, 24) known as a contact surface, intended to be in contact with a vertebral plate of one of the vertebrae between which the prosthesis is intended to be inserted. The geometric centre will hereafter be defined in relation to this contact surface for the sake of ease but it must be understood that it is the vertical axis passing through the geometric centre which matters in the principle of the invention and that the exact position of the geometric centre on the width of the plates has no relevance. In the different embodiments described below, each of the plates (1, 2) therefore comprises a geometric centre (G1, G2) at equal distance from at least two diametrically opposite points located on the periphery of the plate (1, 2). The geometric centres (G1, G2) of the plates (1, 2) are not vertically aligned and this off-set (D) of the geometrical centres (G1, G2) of the plates engenders an off-set of the edges of the plates (1, 2) in at least one direction perpendicular to the vertical axis of the spinal column.

Figure 2A:
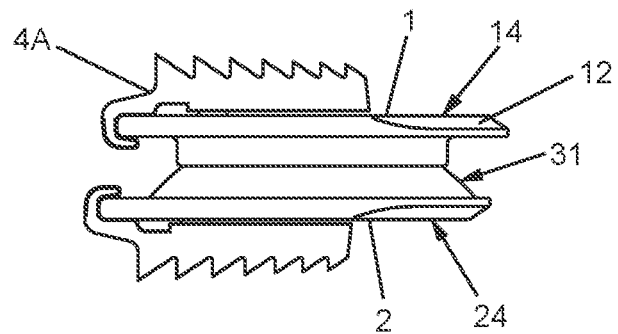
Figure 2B:
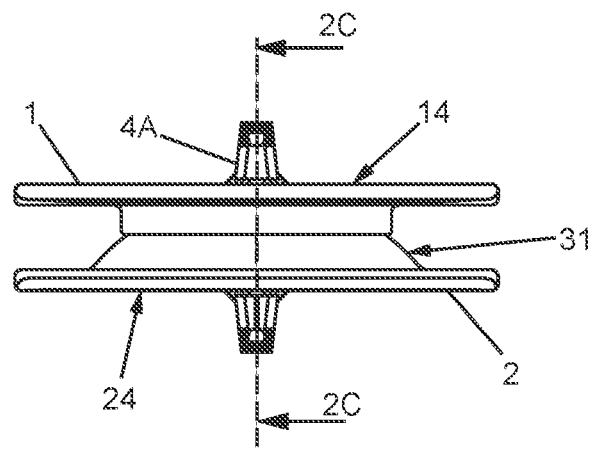
Figure 2C:
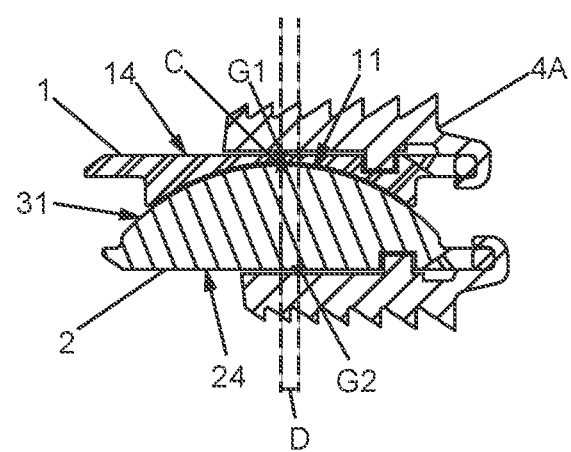
Figure 3A:
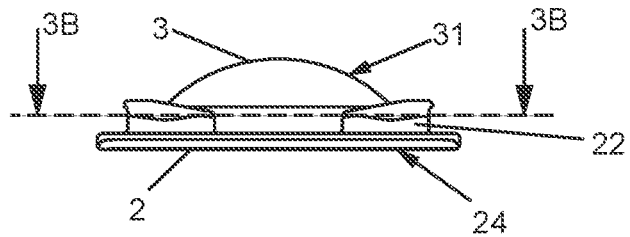
Figure 3B:
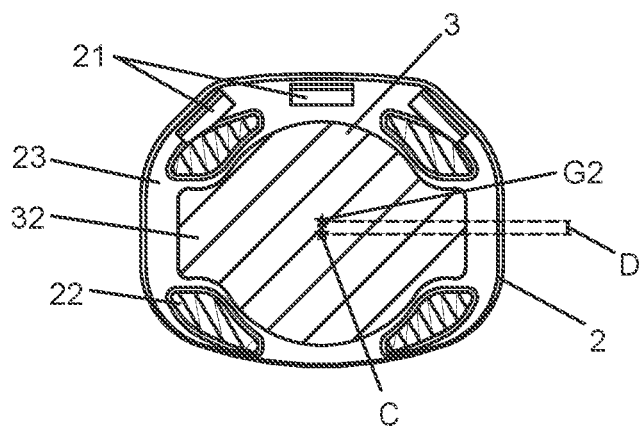
Figure 3C:
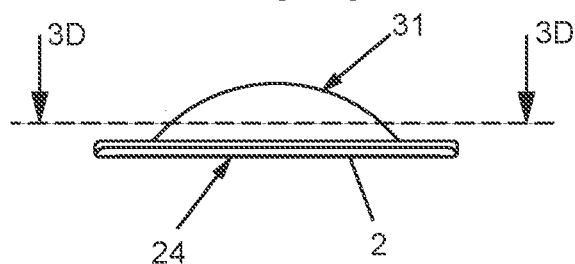
Figure 3D:
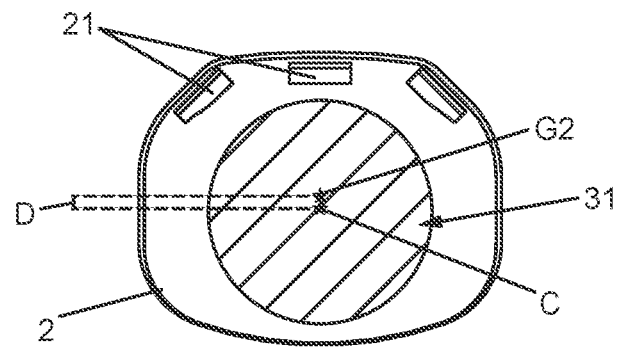
Figure 4A:
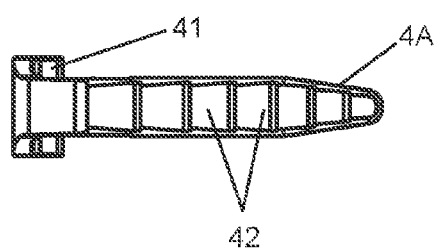
Figure 4B:
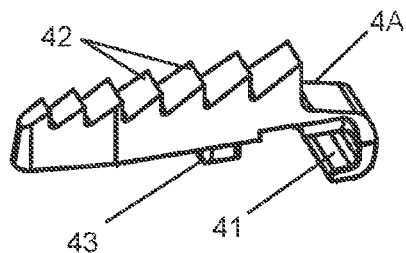
Figure 4C:
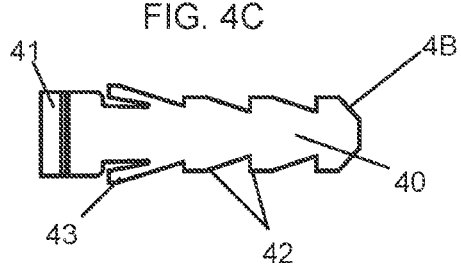
Figure 4D:
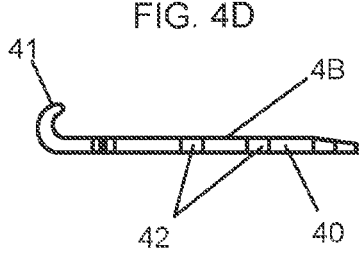

In the embodiment represented in FIGS. 2A, 2B, 2C, 3C and 3D, the prosthesis only comprises two elements: two plates (1, 2). In this case, the second plate (2) comprises a curved surface (31) of articulation of which at least one section co-operates with a curved surface (11) of articulation of the first plate (1) to which it is complementary. The co-operating of these curved surfaces (11, 31) of articulation allows to pivot and/or tilt the plates (1, 2) about each other. A centre (C) of articulation vertically aligned with the vertex of the curved surface (31) of articulation of the second plate (2) can be defined. This centre (C) of articulation corresponds to the mid-position of the centre of the curved surface (11) of the first plate (1) compared to the second plate (2). In the embodiment represented in the figures, the curved surface (11) of the first plate (1) is concave and the curved surface (31) of articulation of the second plate (2) is convex but it can be the case that the curved surface (11) of the first plate (1) is convex and that the curved surface (31) of articulation of the second plate (2) is concave.

Figure 1B:
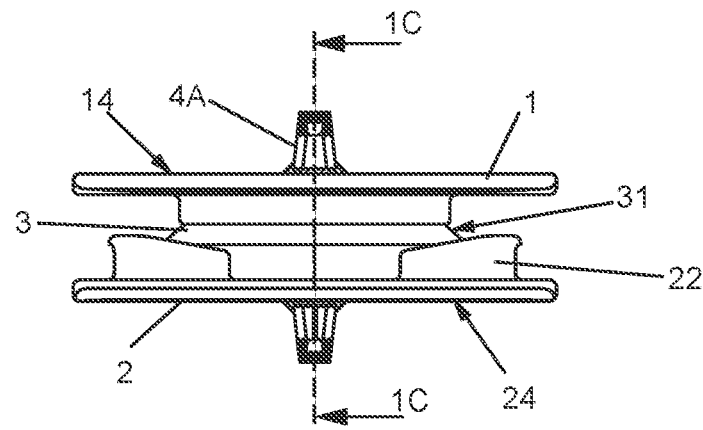
Figure 1C:
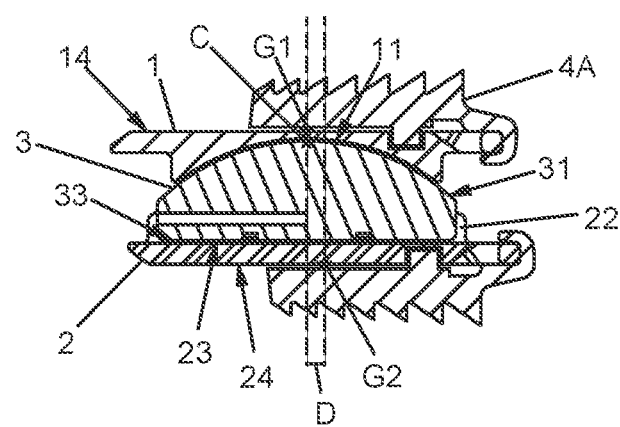
Figure 5A:
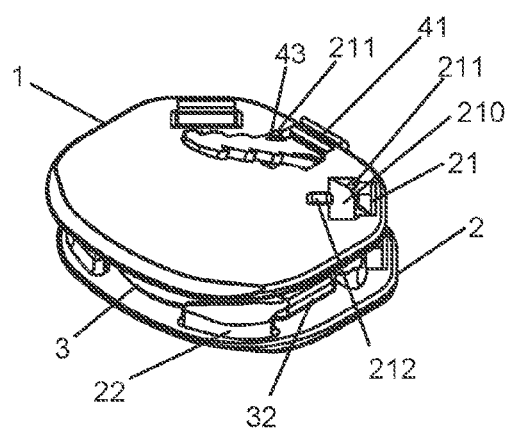
Figure 5B:
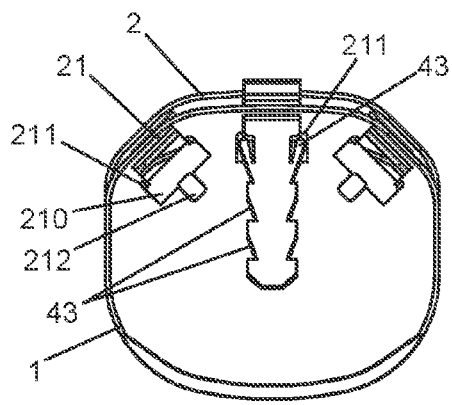
Figure 5C:
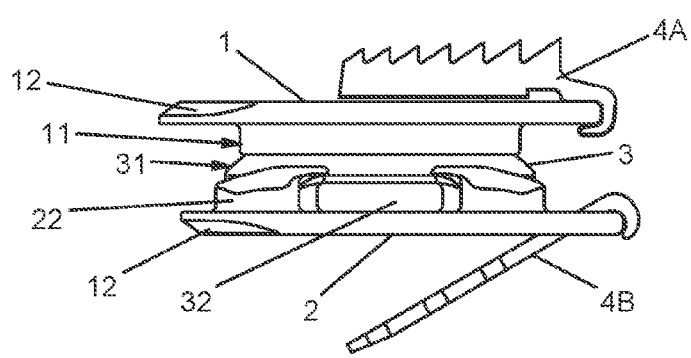

In the embodiment represented in FIGS. 1A to 1C, 3A, 3B and 5A to 5C, the prosthesis also comprises a core (3) comprising a plane surface (33) and a curved surface (31) of articulation. In the case of a prosthesis with three elements, only the first plate (1) comprises a curved surface of articulation (11) and this surface co-operates with at least a section of the curved surface (31) of the core (3) to which it is complementary, to allow to pivot and/or tilt the plates (1, 2) about each other. The plane surface (33) of the core (3) co-operates with at least a section of a plane surface (23) of the second plate (2) to allow a translation of the core (3) in relation to the second plate (2) in at least one direction perpendicular to the vertical axis of the spinal column and/or a rotation of the core (3) in relation to the second plate (2) via rotation about an axis substantially perpendicular to the plane of these plane surfaces. The second plate (2) comprises means for co-operating (22) which are complementary with means for co-operating (32) of the core (3) so as to restrict or abolish at least this translation of the core (3) in relation to the second plate (2). In the embodiments represented in figures, the means for co-operating (22) of the second plate (2) are female means located in the vicinity of the edges of the second plate (2) and co-operating with the male means (32) of the core (3). In the embodiments represented in the figures, these male means for co-operating (32) of the core (3) are two studs located on the two side edges of the core (3) and the female means for co-operating (22) of the second plate (2) are four walls located, in pairs, on each of the two side edges of the second plate (2). These walls comprise an inward curving section towards the centre of the plate (2) and partially covering the male means for co-operating (32) of the core (3) so as to prevent the core (3) from lifting. In another embodiment of the invention, the means for co-operating (22) of the second plate (2) can be male means located in the vicinity of the edges of the second plate (2) and co-operating with the female means (32) of the core (3). In an embodiment of the invention, the dimensions of each male means for co-operating (32, 22) can be slightly smaller than those of the female means for co-operating (22, 32) so as to allow a slight travel between the core (3) and the second plate (2) around the position corresponding to the vertical projection of the centre (C) of articulation. In another embodiment, the dimensions of each male means for co-operating (32, 22) can be substantially identical to those of each female means for co-operating (22, 32) so as to prevent any travel between the core (3) and the second plate (2) and to retain the core (3) in the position corresponding to the vertical projection of the centre (C) of articulation.

In this case of a prosthesis with three elements, the centre (C) of articulation is vertically aligned with the vertex of the curved surface (31) of articulation of the core (3) and correspond to the mid-position of the core (3) between the means for co-operating (22) of the second plate (2) and to the mid-position of the centre of the curved surface (11) of the first plate (1) in relation to the core (3). In the embodiment represented in the figures, the curved surface (11) of the first plate (1) is concave and the curved surface (31) of the core (3) is convex but it could be that the curved surface (11) of the first plate (1) is convex and that the curved surface (31) of the core (3) is concave.

In an embodiment of the invention, the centre (C) of articulation is vertically aligned with the centre (G1) of geometry of the first plate (1) but off-set in relation to the geometric centre (G2) of the second plate (2) in at least a direction perpendicular to the vertical axis of the spinal column. This off-setting (D) of the geometric centres (G1, G2) of the plates engenders an off-setting of the edges of the plates (1, 2) in at least one direction perpendicular to the vertical axis of the spinal column. In another embodiment of the invention, the centre (C) of articulation can also be off-set in relation to the geometric centre (G1) of the first plate (1). This off-setting of the centre (C) of articulation in relation to the geometric centre (G1) of the first plate (1) can be in the opposite direction to that of its off-setting (D) in relation to the geometric centre (G2) of the second plate (2) so that the vertical projection of the centre (C) of articulation lies between the vertical projections of the geometric centres (G1, G2) of the plates (1, 2) and so that the off-setting of the geometric centres (G1, G2) in relation to the centre (C) of articulation cumulate and engender an off-setting of the edges of the plates (1, 2) in at least one direction perpendicular to the vertical axis of the spinal column. This off-setting of the centre (C) of articulation in relation to the geometric centre (G1) of the first plate (1) can also be in the same direction as that of its off-setting (D) in relation to the geometric centre (G2) of the second plate (2), but at a lesser distance so that these off-settings partially compensate each other and engender an off-setting of the edges of the plates (1, 2) between themselves in at least one direction perpendicular to the vertical axis of the spinal column.

It can be beneficial that prostheses according to various embodiments of the invention allow correction of the slope defects of the adjacent vertebrae. The median planes representing the contact surfaces (14, 24) of the plates (1, 2) can therefore be substantially parallel or create an acute angle. The slope obtained by such an angle will allow the overall shape of the prosthesis to be adapted to the anatomy of the spinal column or to correct any possible slope defects of the vertebrae of the patient for whom the prosthesis is intended. The same plates (1, 2) are assembled with core (3) of different thicknesses and/or dimensions and/or shapes. The plates (1, 2) can comprise, at least on their anterior edge, at least a bevel (12) facilitating the insertion of the prosthesis between the vertebrae.

An embodiment of a prosthesis according to the invention comprises mobile osseous anchorage means (4A, 4B) allowing to anchor the plates (1, 2) in the vertebrae. These osseous anchorage means (4A, 4B) and/or the plates (1, 2) can thus comprise means for securing (43 and/or 211, 212) of the binding of the osseous anchorage means (4A, 4B) on the plates (1, 2).

In one embodiment of the mobile osseous anchorage means (4B), at least a plate (40), equipped with notches (42) oriented so as to prevent this notched plate (40) from falling out once inserted in a vertebra, is intended to be interlocked on to at least one edge (21) of an opening in the vicinity of the periphery of the plates (1, 2), thanks to an inwardly curved section (41). Thus, these mobile osseous anchorage means (4B) can be inserted into the vertebrae and interlocked on to the plates of the prosthesis once the latter has been inserted between the vertebrae. This embodiment of the mobile osseous anchorage means (4B) allows a possible adjustment of the position of the prosthesis between the vertebrae prior to definitive bonding. The end of the notched plate (40) opposite the one with an inwardly curved section (41) can comprise a bevel allowing to facilitate the insertion of the notched plate (40) into the vertebrae. The opening in the vicinity of the periphery of the plates (1, 2) can comprise a sloping section (210) on to which the notched plate (40) leans when the curved section (41) of the osseous anchorage means (4B) is interlocked on to the edge (21) of this opening. This sloping section (210) allows to set the angle of the osseous anchorage means (4B) in relation to the plates and to guide them when they are being inserted into the opening. The means for securing (43) can consist of flexible tabs (43) oriented towards the curved section (41) of the osseous anchorage means (4B) and intended to fold back against the edges of the plate (40) when inserting the osseous anchorage means (4B) into the openings in the plates (1, 2).

During the interlocking of the curved sections (41) onto the edges (21) of the openings in the plates (1, 2), these flexible tabs (43) separate to lean against the limit stops (211) located on the walls of the openings in the plates (1, 2), so as to prevent the osseous anchorage means (4B) from falling out. In an alternative embodiment, the inwardly curved section (41) of the notched plate (40) of the mobile osseous anchorage means (4B) extends via a second plate also equipped with notches (42) oriented so as to prevent the plate from falling out once inserted into the vertebrae.

In another embodiment the mobile osseous anchorage means (4A, 4B) of the plates (1, 2) includes at least one winglet (4A) equipped with notches (42) oriented so as to prevent the winglet (4A) from falling out once inserted into a groove made in a vertebra. One end of the winglet (4A) has an inwardly curved section (41) intended to be interlocked on to at least one edge (21) of an opening in the vicinity of the periphery of the plates (1, 2). The means for securing (43) of the winglet (4A) can thus comprise at least a stud (43) located on the lower surface of the winglet (4A) and intended to be interlocked into at least one hole (210) on the contact surfaces (14, 24) of the plates (1, 2). The stud (43) and the hole (210) will be of complementary shape and size so as to secure the winglet (4A) on to the plates (1, 2). In this embodiment, the vertebrae, between which the prosthesis is intended to be inserted, will have been previously prepared by the surgeon by hollowing out, in the vertebral plates, grooves of complementary shape and size with the shape and size of the winglets (4A).

It should be obvious for those skilled in the art that the invention allows embodiments under numerous other specific forms whilst remaining within the scope of the invention as claimed. Consequently, the embodiments should be considered as purely illustrative, but can be modified in the field defined by the impact of the attached claims, and the invention should not be restricted to the aforementioned details.

The invention claimed is:

1. A combination comprising:
   a first elongated anchor having
     a first end configured to facilitate insertion of the anchor into a vertebra,
     a plate-like body with notches configured to facilitate retention of the first elongated anchor in the vertebra,
     a retainer for an intervertebral device located at the second end, and
     a locking tab located between the first end and the second end, proximal to the second end; and
   an intervertebral device having
     a first side having a surface configured for contacting a first vertebra,
     a second side having a surface configured for contacting a second vertebra,
     a first end having a bevel configured to facilitate insertion of the device into the space between the first and second vertebrae,
     a second end located on the opposite side of the device from the first end, and
     a first angled opening along the second end having a sloping section configured to receive the first elongated anchor, to guide the first elongated anchor during insertion of the anchor into a vertebra, and to set the angle of the first elongated anchor with respect to one of the first and second sides of the device.

2. The combination of claim 1 in which the first end of the first elongated anchor is beveled.

3. The combination of claim 1 in which the first elongated anchor comprises a curved portion.

4. The anchor of claim 3 in which the curved portion comprises the retainer.

5. The combination of claim 1 in which the retainer comprises an interlock.

6. The combination of claim 1 in which the locking tab is resilient.

7. The combination of claim 6 in which the locking tab has an insertion position in which the locking tab is compressed and a locking position in which the locking tab is relaxed.

8. The combination of claim 1 in which the device comprises a stop configured to engage the locking tab and lock the first elongated anchor against the device.

* * * * *